United States Patent

Rovati et al.

[11] Patent Number: 4,791,215
[45] Date of Patent: Dec. 13, 1988

[54] DERIVATIVES OF GLUTAMIC ACID AND ASPARTIC ACID

[75] Inventors: Luigi Rovati; Francesco Makovec; Rolando Chiste'; Paolo Senin, all of Monza, Italy

[73] Assignee: Rotta Research Laboratorium S.p.A., Milan, Italy

[21] Appl. No.: 746,065

[22] Filed: Jun. 18, 1985

[30] Foreign Application Priority Data

Jun. 25, 1984 [IT] Italy ............................ 67644 A/84
Oct. 26, 1984 [IT] Italy ............................ 68070 A/84

[51] Int. Cl.$^4$ .................. C07C 121/52; A61K 31/275
[52] U.S. Cl. .................................. 558/415; 544/176; 546/245; 562/433; 562/443; 564/450
[58] Field of Search ............... 558/415; 562/433, 443; 544/176; 546/245; 564/450

[56] References Cited

U.S. PATENT DOCUMENTS 3,551,419 12/1970 Re et al. ............................ 562/540

FOREIGN PATENT DOCUMENTS 14421 2/1974 Japan .................................. 562/450

OTHER PUBLICATIONS

Unverified English translation of Japanese 14421, 1974.

Primary Examiner—Anton H. Sutto
Attorney, Agent, or Firm—Saidman, Sterne, Kessler & Goldstein

[57] ABSTRACT

New derivatives of D,L-glutamic acid and D,L-aspartic acid are described having the formulae:

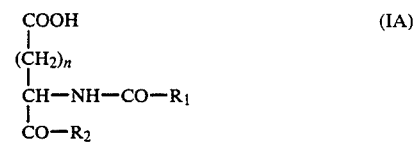

(IA)

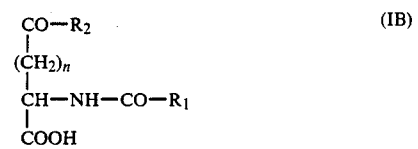

(IB)

in which n is equal to 1 or 2, $R_1$ is a phenyl group mono-, di- or tri-substituted with linear or branched $C_1$-$C_4$ alkyl groups, which may be the same or different, or with halogens, with a cyano group or a trifluoromethyl group, and in which $R_2$ is selected from the group consisting of morpholino, piperidino and amino with one or two linear, branched or cyclic alkyl group substituents containing from 1 to 8 carbon atoms, which may be the same or different, or a pharmaceutically-acceptable salt thereof.

The compounds have an antagonistic activity towards bioactive polypeptides and are useful particularly in the treatment of illnesses of the digestive system and the central nervous system, as pain killers, and for the treatment of anorexia and all those affections (for example tumours) in which exogenous or endogenous bioactive polypeptides are involved.

6 Claims, No Drawings

DERIVATIVES OF GLUTAMIC ACID AND ASPARTIC ACID

FIELD OF THE INVENTION

The invention relates to new derivatives of D,L-glutamic acid and D,L-aspartic acid that have antagonistic activity toward exogenous or endogenous bioactive polypeptides.

SUMMARY OF THE INVENTION

The present invention relates to new derivatives of D,L-glutamic acid and D,L-aspartic acid having the formulae:

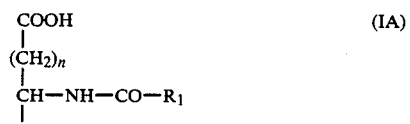

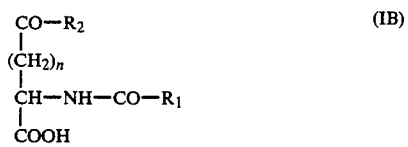

in which n is equal to 1 or 2, $R_1$ is a phenyl group mono-, di- or tri-substituted with linear or branched $C_1$-$C_4$ alkyl groups, which may be the same or different, or with halogens, with a cyano group or a trifluoromethyl group, and in which $R_2$ is selected from the group consisting of morpholino, piperidino and amino with one or two linear, branched or cyclic alkyl group substituents containing from 1 to 8 carbon atoms, which may be the same or different, or a pharmaceutically-acceptable salt thereof.

The compounds have an antagonistic activity towards bioactive polypeptides and are useful particularly in the treatment of illnesses of the digestive system and the central nervous system, as pain killers, and for the treatment of anorexia and those affections in which exogenous or endogenous bioactive polypeptides are involved.

DETAILED DESCRIPTION OF THE INVENTION

The present invention relates to original derivatives of D,L-glutamic acid and D,L-aspartic acid which may be represented by the general formulae indicated below:

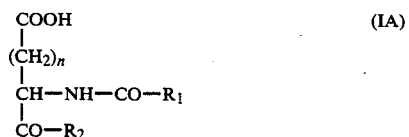

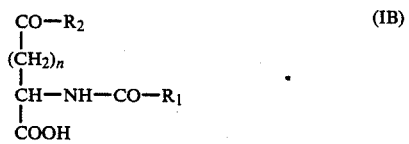

in which n is equal to 1 or 2, $R_1$ is a phenyl group mono-, di- or tri-substituted with linear or branched $C_1$-$C_4$ alkyl groups, which may be the same or different, or with halogens, with a cyano group or a trifluoromethyl group, and in which $R_2$ is selected from the group consisting of morpholino, piperidino and amino with one or two linear, branched or cyclic alkyl group substituents containing from 1 to 8 carbon atoms, which may be the same or different.

The compounds which are the subject of the present invention have been shown to possess interesting pharmocological properties with regard to mammals. One of these properties is a capacity to potentiate the analgesic activity of morphine and other analgesic drugs.

These properties may be at least partly interpreted as due to a powerful antagonistic activity towards cholecystokinin (CCK) or other bioregulating peptides displayed by many of the compounds in question.

The compounds according to the invention may thus be used, to advantage, in the treatment of various human illnesses, such as illnesses of the digestive system, such as, for example, in the treatment of colitis and and biliary diskinesia; or may be used for the treatment of pain of any etiology and intensity.

On the basis of the pharmacological characteristics, one might also predict their use in the treatment of psychic disturbances which can be imputed to imbalances in the physiological neuron levels of CCK or other bioactive polypeptides, and also in the treatment of anorexia, the favouring of weight increase in farm animals or for the treatment of affections in which there is a pathological cellular growth mediated by bioactive peptides (probably such as tumors).

The compounds of the invention, as already mentioned above, have a powerful anti-CCK activity on various experimental models, both in vitro and in vivo. Thus they reduce contractions induced by CCK in the gall bladder of guinea pigs both in vitro and in vivo, they inhibit induced contractions of the colon in rabbits, and they increase biliary secretion in rats.

Of interest also is the potentiation effect on the analgesic activity of analgesic-narcotic and non-narcotic drugs.

This potentiation in fact, in the first place, allows the posology of the opiates to be reduced considerably, thus limiting their multitude of well known, undesirable side effects, without thereby reducing their therapeutic index considerably. These compounds may also be used to re-establish the analgesic activity of opiate drugs when their pharmological effect has fallen off as a result of the well known phenomenon of tolerance, without the need to increase the therapeutic dose. These favourable therapeutic characteristics could thus also serve to enable the gradual detoxification of subjects who have become addicted from the prolonged use of opiate drugs.

In the case of non-narcotic analgesics, their beneficial action goes beyond that of increasing the analgesic activity, which is in itself useful, in that they also protect the gastric mucous membrane which is normally damaged by such products.

This potentiation of the activity of analgesic drugs is, among other things, correlated with the capacity of the compounds according to the invention to block the hydrolytic degradation of enkephalins, endogenous physiological peptides having powerful analgesic activities. This would give the enkephalins themselves a greater half-life and, by definition, a greater activity.

Pharmaceutical forms of the compounds of the invention may be prepared by conventional methods as, for example, tablets, capsules, suspensions, solutions and suppositories, and may be administered orally, parenterally or via the rectum.

The active ingredient is administered to the patient typically in quantities of from 0.1 to 10 mg/kg body weight per dose.

For parenteral administration it is preferable to use a water-soluble salt of the compounds in question, such as the sodium salt or another non-toxic, pharmaceutically-acceptable salt. Substances commonly used in the pharmaceutical industry as excipients, binders, flavouring agents, dispersants, colouring agents, humectants etc. may be used as inactive ingredients.

The method for the preparation of the glutamic acid and aspartic acid derivatives of the invention is characterised in that it includes the step of:

(a) reacting an internal anhydride having the formula:

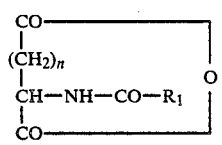

in which n and $R_1$ have the meanings given above, with an amine of formula $R_2H$, in which $R_2$ has the meaning given above, in a molar ratio of from 1 to 5 at a temperature of from $-20°$ C. to $30°$ C., the compounds (IA) and (IB) being recovered from the reaction mass and the compounds (IA) and (IB) being separated.

Preferably, the temperature of the reaction is from $-10°$ C. to $10°$ C.

The internal anhydrides of formula (II) are new compounds which have not been made up till now.

The internal anhydrides (II) are made by the steps of:

(b) reacting glutamic acid or aspartic acid under Schotten-Bauman conditions with an equi-molecular quantity of an acyl chloride of formula $R_1$—CO—Cl, in which $R_1$ has the meaning given above, at a temperature of from $-20°$ C. to $30°$ C. to obtain the N-acylated compound of formula:

$$\begin{array}{l} \text{COOH} \\ | \\ (\text{CH}_2)_n \\ | \\ \text{CH}—\text{NH}—\text{CO}—R_1 \\ | \\ \text{COOH} \end{array} \quad (\text{III})$$

and (c) dehydrating the compound of formula (III) by reaction in the presence of acetic anhydride in a molar ratio of from 1 to 10, either alone or in the presence of an inert solvent miscible therewith, at a temperature of from $-10°$ C. to that of reflux.

The series of steps of the method according to the invention is illustrated in its entirety in the reaction scheme below:

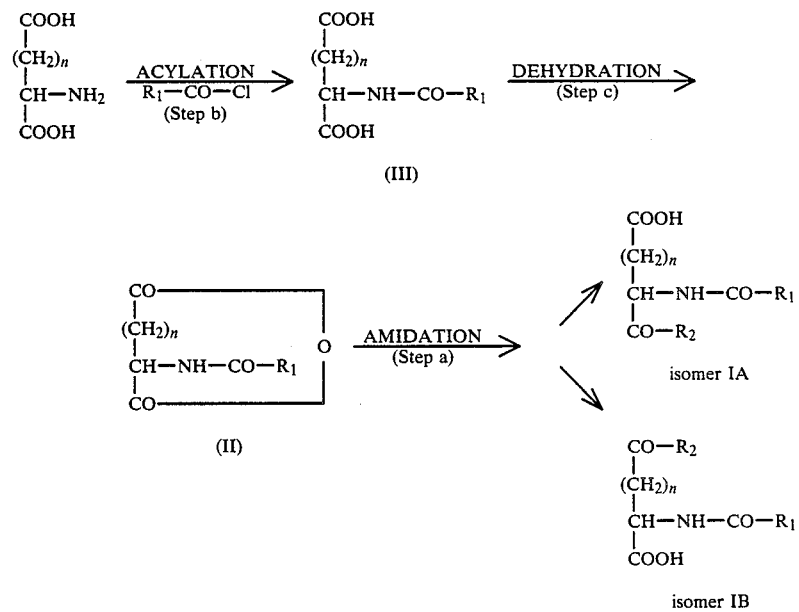

The acylation step (b) is preferably carried out at a temperature of from $0°$ C. to $15°$ C. for a period of from 1 to 24 hours, a temperature of about $5°$ C. and a reaction time of 12 hours is to be recommended.

In step (c) the reaction time is typically from about 30 minutes to 12 hours, preferably about 3 hours, and the quantity of acetic anhydride is preferably 3 moles per mole of compound (III).

In the amidation step (a), the amine of formula $R_2H$ is preferably introduced in a molar ratio of 2.5 to 1 with respect to the internal anhydride (II) and the reaction is carried out for a period of from about 30 minutes to 12 hours, preferably 3 hours.

The relative percentages of the compounds of formulae IA and IB are a function of the type of $R_1$ and $R_2$ substituents used.

The isomers IA and IB may be separated either by fractional crystallisation (with the solvents indicated in Tables (C) and (D) or by extraction in a basic medium, the compounds of formula IB being on average more acid.

The following examples are given better to illustrate the invention.

EXAMPLE 1

TABLE A

D,L-N—acyl derivatives of glutamic and aspartic acids:

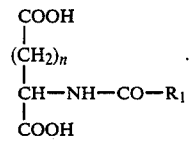

| COM-POUNDS | n | $R_1$ | MELTING POINT (°C.) | SOLVENT OF CRYSTALLIZATION | Rf | YIELD (%) | FORMULA |
|---|---|---|---|---|---|---|---|
| A-1 | 2 | 2-chloro-phenyl | 116–8 | $H_2O$ | 0.32 | 76.5 | $C_{12}H_{12}ClNO_5$ |
| A-2 | 2 | 3-chloro-phenyl | 134–8 | $H_2O$ | 0.40 | 80.3 | $C_{12}H_{12}ClNO_5$ |
| A-3 | 2 | 4-chloro-phenyl | 105–7 | $H_2O$ | 0.44 | 84.7 | $C_{12}H_{12}ClNO_5$ |
| A-4 | 2 | 3,4-dichloro-phenyl | 141–5 | $H_2O$ | 0.46 | 76.4 | $C_{12}H_{11}Cl_2NO_5$ |
| A-5 | 2 | 3,5-dichloro-phenyl | 147–9 | $H_2O$ | 0.48 | 90.1 | $C_{12}H_{11}Cl_2NO_5$ |
| A-6 | 2 | 2,4-dichloro-phenyl | 125–7 | $H_2O$ | 0.43 | 58.5 | $C_{12}H_{11}Cl_2NO_5$ |
| A-7 | 2 | 3,4,5-trichloro-phenyl | 143–5 | $H_2O$/alcohol 1:1 | 0.46 | 85.7 | $C_{12}H_{10}Cl_3NO_5$ |
| A-8 | 1 | 3,4-dichloro-phenyl | 158–61 | $H_2O$ | 0.38 | 86.6 | $C_{11}H_9Cl_2NO_5$ |
| A-9 | 2 | 4-fluoro-phenyl | 84–86 | — | 0.37 | 79.5 | $C_{12}H_{12}FNO_5$ |
| A-10 | 2 | 3,5-difluoro-phenyl | 148–51 | $H_2O$ | 0.41 | 85.5 | $C_{12}H_{11}F_2NO_5$ |
| A-11 | 2 | 2-bromo-phenyl | 127–9 | $H_2O$ | 0.33 | 93.1 | $C_{12}H_{12}BrNO_5$ |
| A-12 | 2 | 4-bromo-phenyl | 148–50 | $H_2O$/alcohol 7:3 | 0.43 | 87.8 | $C_{12}H_{12}BrNO_5$ |
| A-13 | 1 | 2-bromo-phenyl | 147–9 | $H_2O$ | 0.19 | 90.2 | $C_{11}H_{10}BrNO_5$ |
| A-14 | 2 | 2-iodo-phenyl | 135–8 | $H_2O$ | 0.35 | 70.5 | $C_{12}H_{12}INO_5$ |
| A-15 | 2 | 4-iodo-phenyl | 171–3 | $H_2O$/alcohol 7:3 | 0.47 | 84.8 | $C_{12}H_{12}INO_5$ |
| A-16 | 2 | 3,4,5-triiodo-phenyl | 180–4 | $H_2O$/alcohol 1:1 | 0.53 | 87.0 | $C_{12}H_{10}I_3NO_5$ |
| A-17 | 2 | 3-cyano-phenyl | 123–6 | $H_2O$ | 0.22 | 81.2 | $C_{13}H_{12}N_2O_5$ |
| A-18 | 1 | 3-cyano-phenyl | 175–9 | $H_2O$ | 0.12 | 86.5 | $C_{12}H_{10}N_2O_5$ |
| A-19 | 2 | 4-cyano-phenyl | oil | — | 0.27 | 71.0 | $C_{13}H_{12}N_2O_5$ |
| A-20 | 2 | 3-methyl-phenyl | 127–8 | $H_2O$ | 0.33 | 80.0 | $C_{13}H_{15}NO_5$ |
| A-21 | 2 | 4-methyl-phenyl | 102–8 | $H_2O$ | 0.34 | 95.0 | $C_{13}H_{15}NO_5$ |
| A-22 | 2 | 3,4-dimethyl-phenyl | 131–3 | $H_2O$/alcohol 7:3 | 0.38 | 85.0 | $C_{14}H_{17}NO_5$ |
| A-23 | 2 | 3,5-dimethyl-phenyl | 153–5 | $H_2O$/alcohol 7:3 | 0.41 | 83.5 | $C_{14}H_{17}NO_5$ |
| A-24 | 2 | 2,4-dimethyl-phenyl | 98–105 | $H_2O$/alcohol 7:3 | 0.38 | 65.8 | $C_{14}H_{17}NO_5$ |
| A-25 | 2 | 2,4,6-trimethyl-phenyl | 170–4 | $H_2O$/alcohol 7:3 | 0.43 | 72.0 | $C_{15}H_{19}NO_5$ |
| A-26 | 2 | 4-ethyl-phenyl | 154–6 | $H_2O$/alcohol 7:3 | 0.38 | 88.6 | $C_{14}H_{17}NO_5$ |
| A-27 | 2 | 4-n-propyl-phenyl | 108–13 | $H_2O$ | 0.41 | 82.3 | $C_{15}H_{19}NO_5$ |
| A-28 | 2 | 4-isopropyl-phenyl | 49–52 | $H_2O$ | 0.37 | 50.8 | $C_{15}H_{19}NO_5$ |
| A-29 | 2 | 4-n-butyl-phenyl | oil | — | 0.43 | 61.5 | $C_{16}H_{21}NO_5$ |
| A-30 | 2 | 4-isobutyl-phenyl | 118–25 | $H_2O$ | 0.40 | 78.0 | $C_{16}H_{21}NO_5$ |
| A-31 | 2 | 4-trifluoromethyl-phenyl | 153–5 | $H_2O$ | 0.30 | 79.0 | $C_{13}H_{12}F_3NO_5$ |

(*) Eluent used: Chloroform–Acetic Acid –$H_2O$ (8-2-0.1)

Preparation of 3,4-dichloro-N-benzoylglutamic acid (Compound A-4)

To a solution containing 14.7 g (0.1 moles) of L-glutamic acid in 200 ml of 1N soda cooled to 5° C. there are added, simultaneously, 100 ml of 1N soda and 21 g (0.1 moles) of 3,4-chlorobenzoyl chloride, with agitation and cooling, over a period of about 30 minutes.

The mixture is left for 12 hours to react. It is made acid to Congo red with concentrated HCl and the precipitate formed is filtered off. The residue is recrystallised from $H_2O$.

Melting point: 141°–145° C. TLC (see note in Table) Rf: 0.46.

24.5 g obtained. Yield 76.4%

All the compounds of formula III are made by the same method (the preceding scheme). The compounds thus obtained are given in Table A below together with several characteristics which identify them, the yields obtained and the solvents used for the crystallisation.

EXAMPLE 2

Preparation of 3,4-dichloro-benzoyl-glutamic anhydride (compound B-4 in Table B)

30.6 g (0.3 moles) of acetic anhydride and 60 ml of isopropyl ether are added to 32.0 g (0.1 moles) of 3,4-dichloro-benzoyl-glutamic acid. The mass is heated under reflux (73°–77° C.) for 2 hours. It is cooled, filtered, washed with a small amount of ether to remove residual acetic anhydride and dried. Thus 27.0 g are obtained. Yield 89.3%. Melting point: 188°–90° C.

All the compounds of formula II are made by the same method (see the scheme). Numerous examples of these compounds are given by way of example in Table B below together with several characteristics which identify them as well as the yields obtained.

TABLE B

Derivatives of N—acyl-glutamic and aspartic anhydrides of formula:

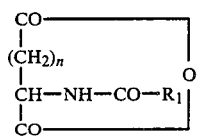

| COMPOUNDS | n | $R_1$ | Melting point (°C.) | Yield (%) | FORMULA |
|---|---|---|---|---|---|
| B-1 | 2 | 2-chloro-phenyl | 129–31 | 79.5 | $C_{12}H_{10}ClNO_4$ |
| B-2 | 2 | 3-chloro-phenyl | 157–8 | 83.8 | $C_{12}H_{10}ClNO_4$ |
| B-3 | 2 | 4-chloro-phenyl | 187–90 | 87.8 | $C_{12}H_{10}ClNO_4$ |
| B-4 | 2 | 3,4-dichloro-phenyl | 188–90 | 89.3 | $C_{12}H_9Cl_2NO_4$ |
| B-5 | 2 | 3,5-dichloro-phenyl | 214–16 | 74.7 | $C_{12}H_8Cl_2NO_4$ |
| B-6 | 2 | 2,4-dichlorophenyl | 155–7 | 74.2 | $C_{12}H_9Cl_2NO_4$ |
| B-7 | 2 | 3,4,5-trichloro-phenyl | 208–10 | 93.3 | $C_{12}H_8Cl_3NO_4$ |
| B-8 | 1 | 3,4-dichloro-phenyl | 195–7 | 91.4 | $C_{11}H_7Cl_2NO_4$ |
| B-9 | 2 | 4-fluoro-phenyl | 171–3 | 72.1 | $C_{12}H_{10}FNO_4$ |
| B-10 | 2 | 3,5-difluoro-phenyl | 198–203 | 91.2 | $C_{12}H_9F_2NO_4$ |
| B-11 | 2 | 2-bromo-phenyl | 147–9 | 72.8 | $C_{12}H_{10}BrNO_4$ |
| B-12 | 2 | 4-bromo-phenyl | 200–3 | 76.9 | $C_{12}H_{10}BrNO_4$ |
| B-13 | 1 | 2-bromo-phenyl | 161–4 | 84.1 | $C_{11}H_8BrNO_4$ |
| B-14 | 2 | 2-iodo-phenyl | 158–60 | 75.6 | $C_{12}H_{10}INO_4$ |
| B-15 | 2 | 4-iodo-phenyl | 201–3 | 88.0 | $C_{12}H_{10}INO_4$ |
| B-16 | 2 | 3,4,5-triiodo-phenyl | 225–8 | 85.2 | $C_{12}H_8I_3NO_4$ |
| B-17 | 2 | 3-cyano-phenyl | 171–3 | 76.7 | $C_{13}H_{10}N_2O_4$ |
| B-18 | 1 | 3-cyano-phenyl | 173–77 | 81.9 | $C_{12}H_8N_4O_4$ |
| B-19 | 2 | 4-cyano-phenyl | 181–5 | 78.8 | $C_{13}H_{10}N_2O_4$ |
| B-20 | 2 | 3-methyl-phenyl | 144–8 | 74.0 | $C_{13}H_{13}NO_4$ |
| B-21 | 2 | 4-methyl-phenyl | 188–90 | 74.2 | $C_{13}H_{13}NO_4$ |
| B-22 | 2 | 3,4-dimethyl-phenyl | 161–3 | 82.5 | $C_{14}H_{15}NO_4$ |
| B-23 | 2 | 3,5-dimethyl-phenyl | 155–7 | 69.0 | $C_{14}H_{15}NO_4$ |
| B-24 | 2 | 2,4-dimethyl-phenyl | 135–8 | 41.2 | $C_{14}H_{15}NO_4$ |
| B-25 | 2 | 2,4,6-trimethyl-phenyl | 160–5 | 38.8 | $C_{15}H_{17}NO_4$ |
| B-26 | 2 | 4-ethyl-phenyl | 174–6 | 78.0 | $C_{14}H_{15}NO_{14}$ |
| B-27 | 2 | 4-n-propyl-phenyl | 159–61 | 72.4 | $C_{15}H_{17}NO_4$ |
| B-28 | 2 | 4-isopropyl-phenyl | 153–5 | 64.5 | $C_{15}H_{17}NO_4$ |
| B-29 | 2 | 4-n-butyl-phenyl | 142–4 | 73.0 | $C_{16}H_{19}NO_4$ |
| B-30 | 2 | 4-isobutyl-phenyl | 139–43 | 72.8 | $C_{16}H_{19}NO_4$ |
| B-31 | 2 | 4-trifluoromethyl-phenyl | 157–9 | 79.0 | $C_{13}H_{10}F_3NO_4$ |

EXAMPLE 3

Preparation of D,L-4-(3,4-dichloro-benzoyl-amino)-5-(di-n-butylamino)-5-oxo-pentanoic acid (Compound C-6 in Table C)

30.2 g (0.1 moles) of 3,4-dichloro-benzoyl-glutamic anhydride are loaded into a reactor and suspended in 100 ml of water. The mass is cooled to about 5° C. and 32.2 g (0.25 moles) of di-n-butylamine are added dropwise over a period of about 15 minutes.

The mixture is left to react for 3 hours at this temperature and acidified with glacial acetic acid. It is filtered, washed with water until it is neutral and dried.

Thus 16.4 g are obtained. Yield 38%. Melting Point: 81°–3° C. (crystallised from isopropyl ether). TLC. Rf: 0.92.

All the compounds of formula IA and IB are made by the same method (see the preceding scheme). Numerous examples of these compounds are given by way of example in the following Tables C and D together with several characteristics which identify them and the yields obtained.

TABLE C

Derivatives of formula:

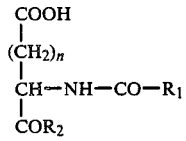

| COMPOUNDS | n | $R_1$ | $R_2$ | Melting Point (°C.) | Solvent of Crystallisation | Rf | Yield (%) |
|---|---|---|---|---|---|---|---|
| C-1 | 2 | 2-chloro-phenyl | di-n-propyl-amino | 133–5 | Ethyl acetate | 0.78 | 53.5 |
| C-2 | 2 | 3-chloro-phenyl | di-n-propyl-amino | 126–8 | Acetone | 0.80 | 17.0 |
| C-3 | 2 | 4-chloro-phenyl | di-n-propyl-amino | 101–3 | $H_2O$/Ethanol 3:7 | 0.88 | 50.0 |
| C-4 | 2 | 4-chloro-phenyl | di-n-pentyl-amino | 104–7 | $H_2O$/Ethanol 1:1 | 0.94 | 24.2 |
| C-5 | 2 | 3,4-dichloro-phenyl | di-n-propyl-amino | 108–10 | Ethyl acetate | 0.87 | 28.0 |
| C-6 | 2 | 3,4-dichloro-phenyl | di-n-butyl-amino | 81–3 | Isopropyl ether | 0.92 | 38.0 |
| C-7 | 2 | 3,4-dichloro-phenyl | di-n-pentyl-amion | 106–8 | Isopropyl ether | 0.95 | 31.7 |
| C-8 | 2 | 3,4-dichloro-phenyl | di-n-hexyl-amino | 108–10 | Isopropyl ether | 0.97 | 21.8 |
| C-9 | 2 | 3,5-dichloro-phenyl | di-n-butyl-amino | 165–7 | $H_2O$/Ethanol 1:4 | 0.95 | 53.4 |
| C-10 | 2 | 2,4-dichloro-pehnyl | di-n-butyl-amino | 124–6 | $H_2O$/Ethanol 1:2 | 0.92 | 57.6 |

TABLE C-continued

Derivatives of formula:

$$\begin{array}{c} COOH \\ | \\ (CH_2)_n \\ | \\ CH-NH-CO-R_1 \\ | \\ COR_2 \end{array}$$

| | n | $R_1$ | $R_2$ | Melting point (°C.) | Solvent for crystallisation | RF(*) | % Yield |
|---|---|---|---|---|---|---|---|
| C-11 | 2 | 3,4,5-trichloro-phenyl | di-n-butyl-amino | 132–4 | H₂O/Ethanol 1:4 | 0.96 | 23.3 |
| C-12 | 2 | 4-fluoro-phenyl | di-n-propyl-amino | 123–5 | H₂O/Ethanol 1:1 | 0.85 | 43.5 |
| C-13 | 2 | 3,5-difluoro-phenyl | di-n-propyl-amino | 132–6 | H₂O/Ethanol 3:7 | 0.88 | 11.4 |
| C-14 | 2 | 2-bromo-phenyl | di-n-propyl-amino | 132–3 | H₂O/Ethanol 1:1 | 0.85 | 54.2 |
| C-15 | 2 | 4-bromo-phenyl | di-n-propyl-amino | 129–31 | Ethyl acetate | 0.83 | 20.7 |
| C-16 | 1 | 2-bromo-phenyl | di-n-propyl-amino | 123–4 | Ethyl acetate | 0.63 | 40.9 |
| C-17 | 2 | 2-iodo-phenyl | di-n-propyl-amino | 146–8 | Ethyl acetate | 0.86 | 25.2 |
| C-18 | 2 | 4-iodo-phenyl | di-n-propyl-amino | 104–11 | Ethyl acetate | 0.83 | 18.3 |
| C-19 | 2 | 3,4,5-triiodo-phenyl | di-n-propyl-amino | 102–5 | H₂O/Ethanol 1:1 | 0.88 | 27.6 |
| C-20 | 2 | 3-cyano-phenyl | di-n-propyl-amino | 120–5 | Ethyl acetate | 0.78 | 37.0 |
| C-21 | 2 | 3-cyano-phenyl | n-butyl-amino | 130–2 | H₂O/Ethanol 1:1 | 0.75 | 28.4 |
| C-22 | 1 | 3-cyano-phenyl | di-n-propyl-amino | 144–5 | Ethyl acetate | 0.63 | 20.0 |
| C-23 | 1 | 3-cyano-phenyl | ciclohexyl-amino | 188–92 | H₂O/Ethanol 3:2 | 0.69 | 90.7 |
| C-24 | 2 | 3-cyano-phenyl | di-n-butyl-amino | 127–9 | H₂O/Ethanol 1:1 | 0.82 | 54.8 |
| C-25 | 2 | 4-bromo-phenyl | di-n-butyl-amino | 120–2 | Isopropyl ether | 0.92 | 27.0 |
| C-26 | 2 | 3,4-dichloro-phenyl | piperidino | 183–5 | Ethyl acetate | 0.74 | 29.4 |
| C-27 | 2 | 4-iodo-phenyl | di-n-butyl-amino | 86–92 | H₂O/Ethanol 1:2 | 0.81 | 39.8 |
| COMPOUNDS | n | $R_1$ | $R_2$ | Melting point (°C.) | Solvent for crystallisation | RF(*) | % Yield |
| C-28 | 2 | 3-methyl-phenyl | di-n-propyl-amino | 132—3 | ethyl acetate | 0.80 | 31.0 |
| C-29 | 2 | 4-methyl-phenyl | " | 137–9 | " | 0.85 | 28.8 |
| C-30 | 2 | 3,4-dimethyl-phenyl | " | 142–4 | " | 0.83 | 44.0 |
| C-31 | 2 | 3,5-dimethyl-phenyl | " | 144–6 | ethanol/water 3:2 | 0.89 | 23.4 |
| C-32 | 2 | 2,4-dimethyl-phenyl | " | 127–9 | ethyl acetate | 0.84 | 50.4 |
| C-33 | 2 | 2,4,6-trimethyl-phenyl | " | 166–8 | " | 0.89 | 39.5 |
| C-34 | 2 | 4-ethyl-phenyl | " | 129–31 | " | 0.86 | 45.7 |
| C-35 | 2 | 4-n-propyl-phenyl | " | 117–9 | ethanol/water 1:1 | 0.82 | 38.3 |
| C-36 | 2 | 4-isopropyl-phenyl | " | 147–150 | methanol/water 7:3 | 0.91 | 48.0 |
| C-37 | 2 | 4-n-butyl-phenyl | " | 126–8 | methanol/water 3:1 | 0.79 | 34.7 |
| C-38 | 2 | 4-isobutyl-phenyl | " | 137–41 | methanol/water 7:3 | 0.85 | 24.5 |
| C-39 | 2 | 4-trifluoromethyl-phenyl | " | 119–21 | ethanol | 0.76 | 37.6 |
| C-40 | 2 | 3,4-dimethyl-phenyl | di-ethyl-amino | 191–2 | ethanol | 0.67 | 65.0 |
| C-41 | 2 | 4-n-propyl-phenyl | " | 133–5 | ethanol/water 1:1 | 0.63 | 46.4 |
| C-42 | 2 | 3,4-dimethyl-phenyl | n-butyl-amino | 155–7 | ethanol/water 7:3 | 0.68 | 21.4 |
| C-43 | 2 | 4-ethyl-phenyl | " | 137–9 | ethanol 95% | 0.68 | 27.6 |
| C-44 | 2 | 4-n-propyl-phenyl | " | 141–4 | ethanol 95% | 0.78 | 11.0 |
| C-45 | 2 | 3,4-dimethyl-phenyl | n-propyl-amino | 155–7 | isopropanol | 0.76 | 20.2 |
| C-46 | 2 | 3,4-dimethyl-phenyl | n-hexyl-amino | 156–8 | acetonitrile | 0.85 | 18.0 |
| C-47 | 2 | 3,4-dimethyl-phenyl | cyclohexyl-amino | 210–2 | methanol | 0.73 | 62.8 |
| C-48 | 2 | 4-ethyl-phenyl | " | 190–2 | methanol | 0.78 | 31.3 |
| C-49 | 2 | 4-isopropyl-phenyl | " | 208–12 | methanol/water 4:1 | 0.82 | 18.6 |
| C-50 | 2 | 3,4-dimethyl-phenyl | dimethyl-amino | 152–4 | water/ethanol 9:1 | 0.37 | 29.0 |
| C-51 | 2 | 3,4-dimethyl-phenyl | morpholine | 147–50 | ethanol | 0.80 | 40.0 |
| C-52 | 2 | 3,4-dimethyl-phenyl | piperidine | 172–4 | methanol | 0.82 | 33.8 |
| C-53 | 2 | 3-methyl-phenyl | di-n-butyl-amino | 92–7 | ethanol/water 1:1 | 0.88 | 12.7 |
| C-54 | 2 | 3,4-dimethyl-phenyl | " | 105–8 | acetonitrile | 0.91 | 13.3 |
| C-55 | 2 | 3,4-dimethyl-phenyl | di-n-pentyl-amino | 109–11 | ethanol/water 1:1 | 0.92 | 40.5 |

(*) Eluent used: isoamyl alcohol-acetone-H₂O (5.2.1)

TABLE D

Derivatives of formula:

$$\begin{array}{c} CO-R_2 \\ | \\ (CH_2)_n \\ | \\ CH-NH-CO-R_1 \\ | \\ COOH \end{array}$$

| COMPOUNDS | n | $R_1$ | $R_2$ | MELTING POINT (°C.) | SOLVENT OF CRYSTALLIZATION | Rf* | YIELD (%) |
|---|---|---|---|---|---|---|---|
| D-1 | 2 | 3,4-dichloro-phenyl | di-methyl-amino | 148–52 | H₂O/Ethanol 3:7 | 0.38 | 30.1 |
| D-2 | 2 | 3,4-dichloro-phenyl | di-n-butyl-amino | 106–8 | H₂O/Ethanol 1:1 | 0.62 | 17.0 |
| D-3 | 1 | 3,4-dichloro-phenyl | n-butyl-amino | 131–4 | H₂O/Ethanol 1:1 | 0.36 | 43.3 |
| D-4 | 2 | 4-bromo-phenyl | di-butyl-amino | 104–7 | Isopropyl ether | 0.50 | 19.9 |
| D-5 | 2 | 3-cyano-phenyl | di-butyl-amino | 115–8 | Ethyl acetate | 0.50 | 28.2 |
| D-6 | 2 | 4-bromo-phenyl | morpholino | 186–9 | H₂O/Ethanol 3:7 | 0.35 | 69.5 |
| D-7 | 2 | 4-bromo-phenyl | piperidino | 132–5 | H₂O/Ethanol 3:7 | 0.35 | 40.8 |

TABLE D-continued

Derivatives of formula:

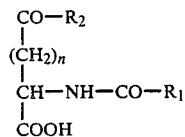

| COMPOUNDS | n | $R_1$ | $R_2$ | MELTING POINT (°C.) | SOLVENT OF CRYSTALLIZATION | Rf* | YIELD (%) |
|---|---|---|---|---|---|---|---|
| D-8  | 2 | 4-cyano-phenyl     | di-butyl-amino   | 112–6   | Ethyl acetate           | 0.51 | 21.3 |
| D-9  | 2 | 3,4-dichloro-phenyl | piperidino       | 101–3   | $H_2O$/Ethanol 1:1      | 0.48 | 29.6 |
| D-10 | 2 | 4-cyano-phenyl     | piperidino       | 177–9   | $H_2O$/Ethanol 3:4      | 0.28 | 37.6 |
| D-11 | 2 | 3-cyano-phenyl     | piperidino       | 106–10  | Ethyl acetate           | 0.22 | 38.9 |
| D-12 | 2 | 3,4-dimethyl phenyl | di-methyl amino  | 204–6   | methanol                | 0.27 | 57.6 |
| D-13 | 2 | 4-ethyl phenyl     | n-butyl amino    | 137–9   | methanol                | 0.48 | 37.5 |
| D-14 | 2 | 4-propyl phenyl    | n-butyl amino    | 138–40  | methanol                | 0.40 | 53.8 |
| D-15 | 2 | 3,4-dimethyl phenyl | di-n-propyl amino | 118–21 | methanol - $H_2O$ (2:1) | 0.47 | 28.8 |
| D-16 | 2 | 3,4-dimethyl phenyl | n-propyl amino   | 167–9   | $H_2O$—acetonitrile (2:1) | 0.44 | 41.5 |
| D-17 | 2 | 4-isopropyl phenyl | piperidine amino | 152–4   | isopropyl alcohol       | 0.34 | 40.3 |

*Eluent used: isoamyl alcohol - acetone - $H_2O$ (5.2.1).

The analgesic activity displayed by the compounds which are the subject of the invention will now be illustrated by a series of pharmacological tests arranged to demonstrate both their potentiation of the analgesic activity of opiates and the mechanism by which this potentiation is achieved.

Experiment No: 1 Increase in analgesia of analgesic-narcotic drugs in rats by the Tail Flick Test The method is that described by Harris et al. (J. Pharmacol. Exp. Ther. 143 (1964) 141–148).

Male rats are used having a weight of about 150–200 g which have not fasted. A point on the tail is chosen and irradiated by a heat source (75° C.) and the time (in seconds) for which the animal remains without moving its tail is measured.

A maximum period of time of 8 seconds under the heat source is chosen, after which the animal is, in any case, removed to avoid tissue damage. The measurement is effected before (controls) and after treatment with the drugs.

The administration of the drugs which are the subject of the invention is carried out intraperitoneally (10 mg/kg) 10 minutes and immediately before administration of morphine (2 mg/kg). The percentage variation is calculated for each individual animal by the following formula:

$$\% \text{ variation} = \frac{\text{Time after treatment (sec)} - \text{control time (sec)}}{8 - \text{control time (sec)}} \times 100$$

The measurements were carried out 10, 20, 30, 45, 60 and 90 minutes after treatment with the analgesics.

The results obtained are given in Table 1 which records the groups treated and the doses administered, the average percentage variations (calculated for groups of 5 animals) of the latency of the pain sensation, the average values calculated for the period 1–90 minutes (±S.E.) and the potency ratio of the morpholine administered alone or together with the compounds which are the subject of the present invention.

From the data given in Table 1 it is seen that, at the tested dose (10 mg/kg i.p.) the products potentiate the activity of morphine up to, for the most active products, an activity of about 3 times that of the morphine alone.

TABLE 1

Activity of the listed compounds of the invention in potentiating the analgesia of opiates in the Tail Flick Test

| Treatment Controls | 10' −10.2 ± 9.3 | 20' 19.6 ± 4.1 | 30' 46.4 ± 8.2 | Times 45' −8.7 ± 13.5 | 60' 18.2 ± 5.1 | 90' 19.9 ± 8.3 | M (10-90) ± SE 14.2 ± 8.6 | Power ratio with respect to morphine alone |
|---|---|---|---|---|---|---|---|---|
| Morphine (M) | 10.8 ± 4.0 | 54.2 ± 17.0 | 46.6 ± 21.0 | 41.7 ± 16.0 | 32.0 ± 17.0 | −6.4 ± 10.0 | 29.8 ± 23.0 | 1 |
| M + C-1 | 65.3 ± 18.0 | 67.2 ± 15.0 | 66.3 ± 14.0 | 82.7 ± 11.0 | 68.8 ± 17.0 | 59.3 ± 25.0 | 68.2 ± 8.0 | 2.29 |
| M + C-2 | 27.8 ± 13.0 | 43.8 ± 25.0 | 67.5 ± 20.0 | 64.2 ± 22.0 | 74.4 ± 16.0 | 57.3 ± 19.0 | 55.8 ± 17.0 | 1.87 |
| M + C-3 | 44.4 ± 23.3 | 83.7 ± 16.3 | 77.8 ± 17.1 | 46.4 ± 24.5 | 73.6 ± 17.7 | 45.8 ± 22.8 | 61.9 ± 18.2 | 2.10 |
| M + C-4 | 44.6 ± 5.3 | 67.5 ± 13.4 | 66.3 ± 14.0 | 60.4 ± 16.3 | 59.8 ± 17.0 | 44.2 ± 14.8 | 57.1 ± 10.3 | 1.92 |
| M + C-5 | 34.5 ± 17.4 | 21.4 ± 16.0 | 59.5 ± 21.1 | 84.7 ± 15.2 | 63.9 ± 18.5 | 40.1 ± 23.9 | 50.7 ± 23.0 | 1.70 |
| M + C-6 | 89.2 ± 6.7 | 91.3 ± 8.7 | 83.6 ± 10.0 | 82.1 ± 16.6 | 79.8 ± 17.0 | 38.2 ± 10.6 | 77.4 ± 19.6 | 2.59 |
| M + C-7 | 67.9 ± 14.3 | 71.5 ± 17.6 | 79.4 ± 10.0 | 84.6 ± 10.5 | 92.9 ± 4.1 | 72.6 ± 7.0 | 78.2 ± 9.4 | 2.62 |
| M + C-8 | 67.4 ± 20.5 | 74.1 ± 15.8 | 80.0 ± 12.9 | 85.9 ± 14.1 | 87.1 ± 12.9 | 60.4 ± 17.3 | 75.8 ± 10.6 | 2.54 |
| M + C-9 | 67.6 ± 11.0 | 65.8 ± 20.0 | 71.9 ± 17.5 | 59.1 ± 20.0 | 52.1 ± 22.0 | 40.4 ± 18.0 | 59.5 ± 11.6 | 2.00 |
| M + C-10 | 56.9 ± 25.8 | 66.4 ± 21.4 | 72.9 ± 16.8 | 70.1 ± 18.5 | 66.2 ± 21.3 | 63.2 ± 23.4 | 66.0 ± 5.6 | 2.21 |
| M + C-11 | 25.2 ± 4.0 | 37.6 ± 16.0 | 50.9 ± 11.0 | 54.4 ± 9.0 | 35.8 ± 5.0 | 18.7 ± 10.0 | 37.1 ± 14.0 | 1.24 |
| M + C-12 | 54.4 ± 16.7 | 76.3 ± 19.0 | 61.6 ± 16.0 | 63.9 ± 20.0 | 65.2 ± 17.0 | 11.6 ± 14.0 | 55.5 ± 22.0 | 1.86 |
| M + C-13 | 24.6 ± 8.9 | 70.0 ± 18.5 | 75.5 ± 15.0 | 56.6 ± 19.5 | 62.3 ± 17.3 | 59.2 ± 25.1 | 58.0 ± 18.0 | 1.95 |
| M + C-14 | 36.5 ± 28.4 | 76.0 ± 12.7 | 79.3 ± 10.6 | 77.0 ± 6.7 | 98.3 ± 1.3 | 71.9 ± 13.2 | 73.1 ± 20.0 | 2.45 |
| M + C-15 | 59.8 ± 14.0 | 84.2 ± 9.6 | 78.3 ± 13.5 | 88.7 ± 8.5 | 82.5 ± 12.7 | 54.5 ± 14.7 | 74.7 ± 14.0 | 2.51 |
| M + C-16 | 43.2 ± 11.0 | 88.7 ± 10.0 | 54.8 ± 5.8 | 47.3 ± 11.8 | 26.1 ± 11.5 | 22.2 ± 16.7 | 47.0 ± 24.0 | 1.58 |
| M + C-17 | 18.9 ± 10.0 | 37.0 ± 12.0 | 45.8 ± 18.0 | 41.0 ± 17.0 | 39.3 ± 20.0 | 31.2 ± 18.0 | 35.5 ± 9.5 | 1.19 |
| M + C-18 | 48.9 ± 31.0 | 65.9 ± 24.0 | 80.1 ± 9.0 | 59.1 ± 20.0 | 33.5 ± 20.0 | 81.4 ± 12.0 | 58.1 ± 15.8 | 1.95 |
| M + C-19 | 3.6 ± 12.0 | 42.8 ± 19.0 | 58.4 ± 21.0 | 66.1 ± 16.0 | 57.1 ± 18.0 | 35.6 ± 20.0 | 43.9 ± 22.7 | 1.47 |
| M + C-20 | 53.8 ± 21.4 | 85.7 ± 17.0 | 92.0 ± 8.0 | 99.1 ± 1.0 | 91.2 ± 9.0 | 51.2 ± 14.0 | 78.8 ± 21.0 | 2.64 |
| M + C-21 | 48.6 ± 19.0 | 37.4 ± 12.0 | 54.8 ± 19.0 | 44.6 ± 15.0 | 64.0 ± 18.0 | 54.9 ± 10.0 | 50.7 ± 9.0 | 1.70 |
| M + C-22 | 82.7 ± 9.4 | 67.6 ± 18.0 | 88.4 ± 9.3 | 83.3 ± 10.5 | 93.6 ± 6.4 | 53.8 ± 14.9 | 78.2 ± 15.0 | 2.62 |
| Morphene (M) | 10.8 ± 4 | 54.2 ± 17 | 46.6 ± 21 | 41.7 ± 16 | 32 ± 17 | −6.4 ± 10 | 29.8 ± 23 | 1 |
| M + C-28 | 15.7 ± 10 | 66.8 ± 18 | 68.3 ± 20 | 68.4 ± 17 | 74.5 ± 11 | 27.5 ± 15 | 53.5 ± 25 | 1.80 |
| M + C-29 | 48.7 ± 20 | 75.5 ± 10.5 | 73.6 ± 11 | 70.0 ± 19 | 47.3 ± 23 | 6.0 ± 14 | 53.5 ± 26 | 1.80 |
| M + C-30 | 69.9 ± 16 | 100.0 ± 0 | 95.2 ± 4.8 | 91.8 ± 8 | 100 ± 0 | 100.0 ± 0 | 92.8 ± 12 | 3.11 |
| M + C-31 | 28.9 ± 17 | 43.3 ± 25 | 54.7 ± 22 | 68.0 ± 22 | 57.4 ± 16 | 49.5 ± 19 | 50.4 ± 14 | 1.69 |
| M + C-32 | 21.8 ± 5 | 58.6 ± 17 | 83.5 ± 10 | 89.8 ± 8 | 78.4 ± 13 | 52.2 ± 22 | 64.0 ± 25 | 2.15 |
| M + C-33 | −0.1 ± 12 | 30.9 ± 8 | 38.7 ± 21 | 41.7 ± 16 | 48.7 ± 21 | 46.6 ± 12 | 34.4 ± 18 | 1.15 |
| M + C-34 | 19.6 ± 23 | 59 ± 17 | 85.5 ± 10 | 78.4 ± 16 | 67 ± 20 | 59.1 ± 23 | 60.6 ± 23 | 2.03 |
| M + C-35 | 39.9 ± 15 | 62.3 ± 23 | 13.7 ± 26 | 63.2 ± 17 | 61.3 ± 20 | 28.8 ± 31 | 44.9 ± 21 | 1.51 |
| M + C-36 | 8.6 ± 13 | 100.0 ± 0 | 96.9 ± 3 | 90.0 ± 10 | 96.9 ± 3 | 92.4 ± 25 | 80.8 ± 36 | 2.71 |
| M + C-37 | 27.6 ± 13 | 45.8 ± 18 | 55.0 ± 16 | 51.1 ± 18 | 23.4 ± 21 | 12.4 ± 13 | 35.9 ± 17 | 1.20 |
| M + C-38 | 53.8 ± 21 | 85.7 ± 10 | 92.0 ± 8 | 99.1 ± 1 | 91.2 ± 9 | 51.1 ± 14 | 78.8 ± 21 | 2.64 |
| M + C-39 | 44.9 ± 15 | 100.0 ± 0 | 93.3 ± 7 | 94.4 ± 6 | 85.6 ± 7 | 81.8 ± 10 | 83.3 ± 20 | 2.79 |
| M + C-40 | 43.8 ± 15 | 69.1 ± 14 | 49.0 ± 25 | 85.6 ± 6 | 76.5 ± 17 | 61.5 ± 14 | 64.2 ± 16 | 2.15 |
| M + C-41 | 32.1 ± 18 | 60.0 ± 22 | 40.0 ± 17 | 46.7 ± 23 | 11.5 ± 11 | 7.4 ± 20 | 32.9 ± 20 | 1.10 |
| M + C-42 | 49.0 ± 31 | 65.9 ± 24 | 80.1 ± 9 | 59.1 ± 20 | 33.5 ± 20 | 61.4 ± 12 | 58.2 ± 16 | 1.95 |
| M + C-43 | 54.1 ± 17 | 44.4 ± 23 | 38.9 ± 26 | 36.8 ± 27 | 47.8 ± 23 | 22.5 ± 13 | 40.7 ± 11 | 1.36 |
| M + C-44 | −1.6 ± 11 | 17.0 ± 10 | 24.9 ± 10 | 26.9 ± 19 | 35.1 ± 17 | 39.8 ± 8 | 23.7 ± 15 | 0.79 |
| M + C-45 | 57.2 ± 18 | 99.7 ± 0.3 | 95.7 ± 4 | 93.1 ± 7 | 77.7 ± 11 | 80.4 ± 9 | 84.0 ± 16 | 2.82 |
| M + C-46 | 14.7 ± 9 | 60.0 ± 18 | 28.0 ± 5 | 55.2 ± 20 | 30.2 ± 8 | 12.2 ± 11 | 32.9 ± 21 | 1.10 |
| M + C-47 | 24.5 ± 14 | 63.5 ± 13 | 52.3 ± 17 | 80.1 ± 22 | 73.2 ± 17 | 49.3 ± 19 | 57.1 ± 20 | 1.92 |
| M + C-48 | 42.1 ± 14 | 59.5 ± 8 | 50.1 ± 21 | 78.4 ± 18 | 43.7 ± 30 | 44.9 ± 18 | 53.1 ± 14 | 1.78 |
| M + C-49 | 62.1 ± 9 | 100.0 ± 0 | 97.6 ± 2 | 99.5 ± 0.5 | 99.2 ± 0.5 | 65.8 ± 0.8 | 87.4 ± 18 | 2.93 |
| M + C-50 | 22.3 ± 13 | 68.9 ± 9 | 60.2 ± 19 | 49.4 ± 14 | 73.5 ± 15 | 24.7 ± 6 | 49.8 ± 22 | 1.67 |
| M + C-51 | 78.7 ± 18 | 82.8 ± 12 | 90.5 ± 10 | 86.4 ± 14 | 65.6 ± 13 | 48.5 ± 10 | 75.4 ± 16 | 2.53 |

TABLE 1-continued

Activity of the listed compounds of the invention in potentiating the analgesia of opiates in the Tail Flick Test

| Treatment Controls | 10' −10.2 ± 9.3 | 20' 19.6 ± 4.1 | 30' 46.4 ± 8.2 | 45' −8.7 ± 13.5 | 60' 18.2 ± 5.1 | 90' 19.9 ± 8.3 | M (10-90) ± SE 14.2 ± 8.6 | Power ratio with respect to morphine alone |
|---|---|---|---|---|---|---|---|---|
| M + C-52 | 72.8 ± 15 | 95.8 ± 3 | 96.3 ± 4 | 85.5 ± 10 | 87.6 ± 8 | 45.3 ± 6 | 80.6 ± 19 | 2.70 |
| M + C-53 | 31.2 ± 15 | 46.7 ± 28 | 70.2 ± 23 | 76.9 ± 22 | 45.6 ± 27 | 12.6 ± 25 | 47.2 ± 24 | 1.58 |
| M + C-54 | 77.0 ± 10 | 89.1 ± 11 | 100 ± 0 | 99.2 ± 0.8 | 69.6 ± 16 | 63.2 ± 19 | 83.0 ± 15 | 2.78 |
| M + C-55 | 89.3 ± 16 | 86.2 ± 12 | 94.4 ± 5 | 100 ± 0 | 100 ± 0 | 81.7 ± 13 | 88.6 ± 12 | 2.97 |
| M + C-23 | 33.1 ± 19.0 | 49.9 ± 15.0 | 58.2 ± 17.0 | 68.3 ± 20.0 | 72.0 ± 18.0 | 58.7 ± 22.0 | 56.7 ± 14.0 | 1.90 |
| M + C-24 | 80.3 ± 13.6 | 87.2 ± 13.0 | 96.9 ± 3.0 | 100.0 ± 0.0 | 74.0 ± 16.0 | 75.3 ± 14.0 | 85.6 ± 11.0 | 2.87 |
| M + C-25 | 59.7 ± 15.0 | 49.0 ± 13.0 | 71.5 ± 13.0 | 61.9 ± 22.0 | 49.0 ± 22.0 | 20.4 ± 6.0 | 51.9 ± 18.0 | 1.74 |
| M + C-26 | 50.1 ± 17.0 | 80.3 ± 20.0 | 84.7 ± 11.0 | 71.8 ± 15.0 | 32.2 ± 7.0 | 4.9 ± 6.0 | 54.0 ± 31.1 | 1.81 |
| M + C-27 | 52.3 ± 13.0 | 81.4 ± 12.0 | 90.2 ± 7.0 | 85.9 ± 10.0 | 60.3 ± 15.0 | 50.3 ± 13.0 | 70.0 ± 17.8 | 2.35 |
| N + D-1 | 75.0 ± 16.0 | 100.0 ± 0.0 | 100.0 ± 0.0 | 86.4 ± 14.0 | 100.0 ± 0.0 | 51.0 ± 21.0 | 85.4 ± 19.7 | 2.86 |
| M + D-2 | 85.6 ± 14.0 | 98.1 ± 2.0 | 95.9 ± 4.0 | 96.6 ± 3.0 | 95.5 ± 3.0 | 87.5 ± 6.0 | 93.2 ± 5.3 | 3.12 |
| M + D-3 | 63.8 ± 17.0 | 79.9 ± 13.0 | 100.0 ± 0.0 | 58.6 ± 18.0 | 33.8 ± 18.0 | 32.9 ± 10.0 | 61.5 ± 26.2 | 2.06 |
| M + D-4 | 72.8 ± 15.0 | 95.8 ± 3.0 | 96.3 ± 4.0 | 85.5 ± 10.0 | 87.5 ± 8.0 | 45.3 ± 6.0 | 80.5 ± 19.3 | 2.70 |
| M + D-5 | 72.2 ± 17.0 | 92.5 ± 7.0 | 95.3 ± 5.0 | 96.0 ± 4.0 | 74.3 ± 11.0 | 75.5 ± 11.0 | 84.3 ± 11.4 | 2.83 |
| M + D-6 | 31.2 ± 22.0 | 45.8 ± 23.0 | 50.7 ± 20.0 | 44.5 ± 24.0 | 45.3 ± 24.0 | 28.2 ± 19.0 | 41.0 ± 9.0 | 1.37 |
| M + D-7 | 31.8 ± 19.0 | 48.0 ± 16.0 | 70.5 ± 15.0 | 73.7 ± 13.0 | 88.6 ± 11.0 | 32.4 ± 19.0 | 57.5 ± 23.5 | 1.93 |
| M + D-8 | 29.0 ± 15.0 | 50.9 ± 8.0 | 61.4 ± 22.0 | 57.7 ± 18.0 | 52.9 ± 20.0 | 28.3 ± 12.0 | 46.7 ± 14.4 | 1.56 |
| M + D-9 | 88.5 ± 19.0 | 74.0 ± 16.0 | 70.9 ± 16.0 | 73.0 ± 15.0 | 84.5 ± 12.0 | 79.9 ± 12.0 | 75.1 ± 6.0 | 2.52 |
| M + D-10 | 41.0 ± 8.0 | 58.6 ± 17.0 | 59.8 ± 17.0 | 62.7 ± 15.0 | 47.0 ± 15.0 | 35.4 ± 11.0 | 50.8 ± 11.2 | 1.70 |
| M + D-11 | 25.3 ± 7.0 | 68.3 ± 20.0 | 74.8 ± 18.0 | 82.8 ± 17.0 | 86.2 ± 14.0 | 77.5 ± 13.0 | 69.1 ± 22.3 | 2.32 |
| M + D-12 | 45.4 ± 23 | 63.9 ± 15 | 84. ± 16 | 100 ± 21 | 78.5 ± 15 | 56.1 ± 22 | 71.3 ± 20 | 2.39 |
| M + D-13 | 7.1 ± 8 | 32 ± 19 | 62.5 ± 23 | 31.8 ± 21 | 48.5 ± 22 | 50.9 ± 14 | 38.8 ± 20 | 1.30 |
| M + D-14 | 69.2 ± 14 | 93.4 ± 7 | 46.8 ± 15 | 71.3 ± 17 | 89.1 ± 9 | 60.3 ± 71.1 ± | 14 ± 2.41 | |
| M + D-15 | 43.5 ± 16 | 48.7 ± 18 | 72.6 ± 19 | 60.1 ± 23 | 59.2 ± 18 | 43.5 ± 24 | 54.6 ± 11 | 1.83 |
| M + D-16 | 29.7 ± 21 | 42.8 ± 18 | 40.1 ± 22 | 35.4 ± 18 | 33.3 ± 20 | 23.3 ± 20 | 34.1 ± 17 | 1.14 |
| M + D-17 | 62.3 ± 15 | 92.9 ± 7 | 100 ± 0 | 100 ± 0 | 100 ± 0 | 100 ± 0 | 92.5 ± 15 | 3.10 |

Experiment No. 2: Hot-plate test
The method is that described by Eddy et al. (J. Pharmac. Exp. Ther. 107, 385 (1953)).

Groups of five male rats having a weight of about 150 g, and which have not fasted, are used.

The animals are placed on a metal plate on the bottom of a transparent cylinder, which is heated to 55°±1° C. by an azeotropic boiling mixture (acetone-ethyl formate 1:1).

The reaction time is defined as the interval which passes between the moment at which the animal is placed on the hot-plate and the moment at which it either licks its feet or tries to jump out of the cylinder. The control reaction time is measured 10 and 5 minutes before administration of the drugs and 10, 20, 30, 45, 60 and 90 minutes afterwards. The animals are left on the plate for a maximum period of 30 seconds.

The response to the administration of the product is considered positive if at least a doubling of the normal reaction time is seen. The results obtained are given in Tables 2a and 2b which record the groups treated, the doses administered and the stay times on the plate expressed as the number of positive responses over the number treated.

TABLE 2a

Power of several compounds which are the subject of the invention to potentiate the activity of analgesic drugs in the hot-plate test.

| TREATMENT | DOSAGE mg/kg i.p. | 10' | 20' | 30' | 45' | 60' | 90' | TOTAL positives x/30 |
|---|---|---|---|---|---|---|---|---|
| Propoxyphene (Pr.) | 15 | 2/5 | 2/5 | 3/5 | 3/5 | 1/5 | 3/5 | 12 |
| Pr + Compound C-20 | 15 + 1 (C-20) | 2/5 | 2/5 | 3/5 | 3/5 | 3/5 | 3/5 | 16 |
| Pr + Compound C-20 | 15 + 3 (C-20) | 3/5 | 5/5 | 4/5 | 5/5 | 4/5 | 4/5 | 25 |
| Pr + Compound C-20 | 15 + 10 (C-20) | 4/5 | 5/5 | 5/5 | 5/5 | 5/5 | 3/5 | 27 |
| Oxyphenylbutazone (Oxy) | 50 | 2/5 | 1/5 | 2/5 | 2/5 | 0/5 | 0/5 | 7 |
| Oxy + Compound D-2 | 50 + 3 (D-2) | 2/5 | 1/5 | 2/5 | 3/5 | 3/5 | 1/5 | 12 |
| Oxy + Compound D-2 | 50 + 10 (D-2) | 1/5 | 1/5 | 3/5 | 3/5 | 2/5 | 2/5 | 12 |
| Oxy + Compound D-2 | 50 + 30 (D-2) | 3/5 | 4/5 | 4/5 | 4/5 | 4/5 | 4/5 | 23 |
| Acetyl Salicylic Acid (ASA) | 100 | 1/5 | 2/5 | 2/5 | 2/5 | 0/5 | 1/5 | 8 |
| Asa + Compound C-20 | 100 + 5 (C-20) | 2/5 | 2/5 | 2/5 | 3/5 | 3/5 | 0/5 | 12 |
| Asa + Compound C-20 | 100 + 20 (C-20) | 1/5 | 3/5 | 3/5 | 3/5 | 4/5 | 3/5 | 17 |
| Asa + Compound C-20 | 100 + 50 (C-20) | 3/5 | 2/5 | 5/5 | 5/5 | 4/5 | 3/5 | 22 |

From the results given in the table it may be seen that even at doses of 3 mg/kg i.p, the compound C-20 can double the analgesic activity of propoxyphene. There is, in practice, a maximum effect at a dose of 10 mg/kg i.p.

TABLE 2b

| TREATMENT | Dosage mg/kg i.p. | 10' | 20' | 30' | 45' | 60' | 90' | Total positives X/30 |
|---|---|---|---|---|---|---|---|---|
| Propoxyphene (Prop.) | 10 | 1/5 | 2/5 | 2/5 | 2/5 | 1/5 | 0/5 | 8 |
| Prop. + Compound C-30 | 10 + 0.3 (C-30) | 2/5 | 1/5 | 3/5 | 3/5 | 2/5 | 0/5 | 11 |
| Prop. + Compound C-30 | 10 + 1 (C-30) | 3/5 | 4/5 | 4/5 | 4/5 | 2/5 | 2/5 | 19 |
| Prop. + Compound C-30 | 10 + 3 (C-30) | 3/5 | 5/5 | 5/5 | 5/5 | 4/5 | 3/5 | 25 |
| Methadone (Met.) | 1 | 1/5 | 2/5 | 1/5 | 2/5 | 1/5 | 1/5 | 8 |
| Met. + Compound C-36 | 1 + 0.3 (C-36) | 2/5 | 2/5 | 3/5 | 3/5 | 1/5 | 1/5 | 2 |
| Met. + Compound C-36 | 1 + 1 (C-36) | 3/5 | 5/5 | 4/5 | 3/5 | 3/5 | 1/5 | 19 |
| Met. + Compound C-36 | 1 + 3 (C-36) | 5/5 | 5/5 | 3/5 | 4/5 | 5/5 | 2/5 | 24 |
| Oxyphenylbutazone (oxy) | 50 | 2/5 | 1/5 | 2/5 | 2/5 | 0/5 | 0/5 | 7 |
| Oxy + Compound C-30 | 50 + 3 (C-30) | 1/5 | 1/5 | 3/5 | 2/5 | 2/5 | 2/5 | 11 |
| Oxy + Compound C-30 | 50 + 10 (C-30) | 1/5 | 2/5 | 2/5 | 3/5 | 3/5 | 2/5 | 12 |
| Oxy + Compound C-30 | 50 + 30 (C-30) | 2/5 | 3/5 | 4/5 | 4/5 | 4/5 | 3/5 | 20 |
| Acetyl Salicylic Acid (Asa) | | | | | | | | |
| Asa + Compound C-36 | 100 | 1/5 | 2/5 | 2/5 | 2/5 | 0.5 | 1/5 | 8 |
| Asa + Compound C-36 | 100 + 10 (C-36) | 1/5 | 2/5 | 3/5 | 2/5 | 1/5 | 1/5 | 10 |
| Asa + Compound C-36 | 100 + 30 (C-36) | 1/5 | 2/5 | 2/5 | 3/5 | 3/5 | 3/5 | 14 |
| Asa + Compound C-36 | 100 + 100 (C-36) | 3/5 | 3/5 | 4/5 | 4/5 | 4/5 | 2/5 | 20 |

From the results given in Table 2b it may be seen that even 1 mg/kg i.p. doses of the compounds in question are capable of at least doubling the analgesic activity of propoxyphene and methadone.

In order to increase the analgesic activity of non-narcotic drugs, higher doses of the drugs of the invention are necessary and the significance is generally comparable at the higher doses.

Experiment No. 3: Influence of several of the compounds of the invention on the analgesic activities of endogenous opiates released by transcutaneous shock in rats and measured by the Tail Flick Test The method is that described by Lewis et al. J. Neurosc. 1, 358 (1961). Male rats which have not fasted and have a weight of about 200 g are used.

The animals are stressed by the application of a 60 Hz–2.5 mA current to the front leg in pulses of a duration of 1 second every 5 seconds for 20 minutes.

This stress regime induces the release of endogenous opiates. Immediately after the electrical stimulation the animals are subjected to the Tail Flick Test at times indicated in the table.

The compounds are administered i.v. immediately before the electric shock at the doses indicated in Table 3.

TABLE 3

Average latency (in sec) determined by the Tail Flick Test at different times (minutes) from the electric shock (average values for groups of 5 animals ± ES).

| TREATMENT | Dose mg/kg iv | Time 5' | 10' | 15' |
|---|---|---|---|---|
| A: Controls | — | −2.88 ± 0.11 | 3.04 ± 0.29 | 2.70 ± 0.27 |
| B: Controls stressed | — | 5.16 ± 0.23 | 3.98 ± 0.203 | 3.10 ± 0.19 |
| tv. A | | 8.74*** | 2.54* | 1.073 |
| C: Compound C-20 + stress | 1 | 7.5 ± 0.3 | 5.34 ± 0.46 | 3.88 ± 0.29 |
| tv. A | | 11.18*** | 4.21** | 2.79* |
| tv. B | | 6.03*** | 2.67 | 2.20 |
| D: Compound C-20 + stress | 3 | 8.48 ± 0.62 | 6.42 ± 0.21 | 4.98 ± 0.36 |
| tv. A | | 8.81*** | 9.23*** | 4.92** |
| tv. B | | 4.97** | 8.77*** | 4.0** |
| E: Compound D-2 + stress | 1 | 9.2 ± 0.53 | 7.0 ± 0.86 | 5.28 ± 0.64 |
| tv. A | | 10.50*** | 4.42** | 3.59** |
| | | 6.94*** | 3.49** | 3.22* |
| F: Compound D-2 + stress | 3 | 9.6 ± 0.46 | 7.24 ± 0.58 | 5.08 ± 0.52 |
| tv. A | | 12.42*** | 6.38*** | 3.97** |
| tv. B | | 8.47** | 5.29** | 3.57** |

Note:
*$P < 0.05$
**$P < 0.01$
***$P < 0.001$

| | | | | |
|---|---|---|---|---|
| G: Compound C-30 + stress | 1 | 7.26 ± 0.52 | 6.10 ± 0.49 | 4.68 ± 0.5 |
| tv. A | | 8.11*** | 5.34** | 3.10** |
| tv. B | | 3.64** | 3.97** | 2.67* |
| H: Compound C-30 + stress | 3 | 9.46 ± 0.64 | 7.96 ± 0.61 | 6.82 ± 0.78 |
| tv. A | | 10.06*** | 7.22*** | 4.95** |
| tv. B | | 6.28*** | 6.14*** | 4.65** |
| I: Compound C-34 + stress | 1 | 5.40 ± 0.35 | 4.9 ± 0.25 | 3.4 ± 0.16 |
| tv. A | | 7.05*** | 4.80** | 2.24 |
| tv. B | | 0.76 | 2.82* | 1.44 |
| L: Compound C-34 + stress | 3 | 6.56 ± 0.33 | 5.58 ± 0.31 | 3.98 ± 0.32 |
| tv. A | | 7.11*** | 5.92*** | 2.92* |
| tv. B | | 3.45** | 4.26** | 2.36* |
| M: Compound C-36 + stress | 1 | 6.9 ± 0.74 | 6.5 ± 0.42 | 4.66 ± 0.55 |
| tv. A | | 5.34*** | 6.72*** | 2.92* |
| tv. B | | 3.31** | 5.36*** | 2.48* |
| N: Compound C-36 + stress | 3 | 9.22 ± 0.67 | 8.1 ± 0.43 | 9.28 ± 0.64 |
| tv. A | | 7.70*** | 9.84*** | 9.30*** |
| tv. B | | 5.66*** | 8.74*** | 9.18*** |
| O: Compound C-39 + stress | 1 | 6.3 ± 0.4 | 5.8 ± 0.38 | 4.04 ± 0.36 |
| tv. A | | 8.21*** | 5.72*** | 2.85* |
| tv. B | | 2.46 | 4.18* | 2.30 |
| P: Compound C-39 + stress | 3 | 7.54 ± 0.65 | 5.98 ± 0.41 | 5.08 ± 0.6 |
| tv. A | | 5.05*** | 5.55*** | 3.51** |
| tv. B | | 4.43** | 4.43** | 3.12* |
| Q: Compound D-17 + stress | 1 | 6.18 ± 0.65 | 7.02 ± 0.76 | 5.31 ± 0.55 |
| tv. A | | 4.97** | 4.90** | 4.16** |
| tv. B | | 1.47 | 3.89** | 3.79** |
| R: Compound D-17 + stress | 3 | 9.08 ± 0.55 | 9.08 ± 0.80 | 6.08 ± 0.98 |
| tv. A | | 10.96*** | 7.02*** | 3.28* |
| tv. B | | 6.52*** | 6.14*** | 2.99* |

Note:
*$P > 0.05$
**$P > 0.01$
***$P > 0.001$

From the data given in the table it is seen that even at doses of 1 mg/kg, the compounds of the invention can increase the analgesic activity of endogenous enkephalins generally to a highly significant extent: this increase is dose-dependent, the effect in fact increasing in both intensity and duration in dependence on the dose.

Experiment No. 4: Potentiation of the analgesic activities of enkephalins induced by some of the compounds of the invention.

In order to check one of the possible mechanisms of the action of the compounds of the invention, that is their possible inhibition of the enzymatic degradation of endogenous enkephalins, the following experiment was carried out: a cannula was implanted in the right lateral ventricle of male rats having a weight of 150-200 g (groups of five animals were used) in order to allow the intracerebroventricular (i.c.v.) administration of drugs according to the method of Noble et al (Life Science 6, (1970) 281-191).

The animals were subsequently treated (i.c.v.) with 3 μg of D-ala-methionine-enkephalinamide (DALA) immediately after an injection (i.c.v.) of the compounds in question at the doses given in Table 4. Analgesia was tested for by the Tail Flick Test already mentioned, at the times given in the Table.

From the data given one can see the potentiating action of the tested components on the analgesic effect of the enkephalinamide (DALA) both in intensity and duration.

This activity, which is highly significant even at doses of 0.01 μg/kg, is probably related to an inhibiting activity on an enzyme (or enzymes) responsible for the metabolism of the enkephalins.

Experiment No. 5: Antagonism of several products of the invention to the development of tolerance induced in rats by the repeated administration of morphine HCl.

Several of the compounds of the invention were examined to determine their possible capacity to antagonise the development of tolerance induced by morphine. Groups of 6 male rats having a weight of about 200-250 grams were used.

At intervals of 24 hours from the first treatment (time 0) each animal (except the control group treated physiologically) received 5 mg/kg of morphine hydrochloride i.p. together with 10 mg/kg i.p. of the compounds indicated (with the exception of the group treated solely with morphine).

The determination of the pain threshold was effected 15', 30', 45' and 60' from the treatment by the Tail Flick Test.

The data given in Table 5 relate to the average values of these four determinations and indicate the percentage variations in the latency time (appearance of pain) before and after treatment with the drugs.

The table also gives the values of Student's t determined at various times for the groups treated with the

TABLE 4

Increase in the analgesic activity of DALA induced by several compounds of the invention determined by the Tail Flick Test in rats.

| GROUP | TREATMENT | Doses | 10' | 20' | 30' | 45' | 60' | 90' | MEAN | Student's |
|---|---|---|---|---|---|---|---|---|---|---|
| | | μg/kg(ICV) | | | | | | | | |
| A | Controls | — | −3.3 ± 4.6 | 0.3 ± 5.2 | 0.9 ± 4.5 | −4.3 ± 5.0 | −3.0 ± 5.5 | −1.1 ± 5.0 | −2.0 ± 2.1 | — |
| B | DALA (D) | 10 | 21.9 ± 20.0 | 25.9 ± 19.2 | 26.2 ± 18.8 | 26.0 ± 19.2 | 7.3 ± 7.1 | 5.0 ± 5.7 | 18.7 ± 9.9 | v. A: 5.07*** |
| C | DALA + Compound C-20 | 10(D) + 0.003 | 5.7 ± 4.4 | 44.6 ± 15.6 | 32.3 ± 14 | 30.1 ± 9.3 | 24.5 ± 7.7 | 72. ± 3.6 | 24.1 ± 13.8 | v. A: 4.20** v. B: 0.72 |
| D | DALA + Compound C-20 | 10(D) + 0.01 | 16.5 ± 4.7 | 62.5 ± 18.7 | 64.1 ± 22.2 40 | 45.4 ± 18.4 | 45.3 ± 20.8 | 16.3 ± 5.8 | 41.7 ± 21.2 | v. A: 5.0*** v. B: 2.41* |
| E | DALA + Compound D-2 | 10(D) + 0.003 | 34.9 ± 24.1 | 54.0 ± 26.7 | 45.5 ± 21.6 | 27.5 ± 15.4 | 23.5 ± 9.2 | 14.9 ± 8.1 | 33.4 + 14.5 | V. A: 5.95*** v. B: 2.05 |
| F | DALA + Compound D-2 | 10(D) + 0.01 | 38.2 ± 18.3 | 53.7 ± 19.8 | 52.6 ± 46.0 | 38.5 ± 16.4 | 33.7 ± 16.9 | 26.3 ± 13.0 | 40.5 ± 9.8 | V. A: 9.59*** v. B: 3.66** |
| | | mg/kg(ICV) | | | | | | | | |
| AA | Controls | — | 0.68 ± 5.45 | 5.64 ± 4.83 | 1.43 ± 4.42 | 4.86 ± 3.90 | 4.21 ± 4.41 | 4.91 ± 2.25 | 3.62 ± 2.05 | — |
| BB | DALA (D) | 10 | 4.1 ± 8.89 | 6.24 ± 4.0 | 59.19 ± 2.92 | 8.29 ± 1.69 | 6.20 ± 2.60 | 10.56 ± 3.87 | 7.51 ± 2.31 | v. A: 3.08* |
| G | DALA + Compound C-30 | 10(D) + 0.01 | 58 ± 15.3 | 60.8 ± 14.2 | 77.0 ± 16.7 | 66.4 ± 12.4 | 48.8 ± 16.2 | 45.0 ± 11.1 | 59.33 ± 11.7 | v. A: 11.5*** v. B: 10.6*** |
| H | DALA + Compound C-30 | 10(D) + 0.01 | 59.1 ± 15.2 | 67.8 ± 16.0 | 56.0 ± 9.5 | 83.3 ± 8.4 | 83.3 ± 6.41 | 55.1 ± 16.2 | 73.26 ± 14.5 | v. A: 11.6*** v. B: 11.0*** |
| I | DALA + Compound D-36 | 10(D) + 0.03 | 41.1 ± 14.7 | 55.6 ± 15.0 | 38.5 ± 19.61 60 | 35.88 ± 14.31 | 32.63 ± 15.89 | 25.44 ± 16.59 | 38.19 ± 10.1 | v. A: 8.2*** v. B: 7.25*** |
| L | DALA + Compound D-36 | 10(D) + 0.03 | 55.82 ± 1.89 | 70.58 ± 18.43 | 53.13 ± 17.63 | 35.17 ± 15.95 | 38.00 ± 13.60 | 20.62 ± 9.35 | 45.55 ± 17.7 | v. A: 5.75*** v. B: 5.2*** |

Note:
*P < 0.05
**P < 0.01
***P < 0.001 drugs in comparison with the control group and the group treated with morphine.

Krebs at a temperature of 32° C. with continuous oxygenation with an oxygen-$CO_2$ mixture (95-5V/V).

TABLE 5

Antagonism of several products of the invention to the development of tolerance induced in rats by the repeated administration of morphine HCl

| TREATMENT | Dose mg/kg ip | Time 0 | Time 24 h | Time 48 h | Time 72 h | Time 96 h | Time 120 h | Time 144 h | Time 168 h |
|---|---|---|---|---|---|---|---|---|---|
| A: Controls | — | −0.73 ± 4.10 | 0.86 ± 1.04 | 5.43 ± 1.18 | 1.09 + 1.90 | 3.97 ± 1.00 | 1.47 + 1.58 | 1.08 ± 3.12 | −0.77 ± 1.08 |
| | | Effect % = −0.0040 · h + 1.89 | | | | | (r = 0.11; t = 0.27 NS) | | |
| B: Morphine | 5 mg/kg + (M) | 58.03 ± 11.20 | 42.09 ± 19.20 | 26.54 ± 15.90 | 19.96 + 7.03 | 10.79 ± 7.05 | 4.45 ± 0.69 | 3.58 ± 3.31 | 2.12 ± 3.47 |
| | | Effect % = −0.327 · h + 48.42 | | | | | (r = 0.95; t = 7.22***) | | |
| C: Compound D-8 | 10 mg/kg + (M) | 47.32 | 43.65 | 32.80 | 31.78 | 35.45 | 42.08 | 29.33 | 19.17 |
| | | Effect % = −0.118 · h + 45.08 | | | | | (r = 0.76; t = 2.89*) | | |
| D: Compound C-20 | 10 mg/kg + (M) | 72.15 | 53.36 | 48.17 | 53.67 | 31.56 | 41.67 | 14.48 | 13.75 |
| | | Effect % = −0.320 · h + 67.97 | | | | | (r = 0.93; t = 6.12***) | | |
| E: Compound D-2 | 10 mg/kg + (M) | 74.14 | 45.73 | 59.50 | 51.52 | 43.40 | 37.60 | 21.43 | 29.75 |
| | | Effect % = −0.251 · h + 66.47 | | | | | (r = 0.89; t = 4.65**) | | |

| TREATMENT | Dose mg/kg ip | Time 0 | Time +24 h | Time +48 h | Time +72 h | Time +96 h | Time +120 h | Time +144 h | Time 168 h |
|---|---|---|---|---|---|---|---|---|---|
| A: Controls | — | −0.73 ± 4.1 | 0.86 ± 1.04 | 5.43 ± 1.18 | 1.09 ± 1.90 | 3.97 ± 1.0 | 1.47 ± 1.58 | 1.08 ± 3.12 | −0.77 ± 1.08 |
| B: Morphine | 5 mg/g + (M) | 58.03 ± 11.2 | 42.09 ± 19.2 | 26.54 ± 15.9 | 19.96 ± 7.03 | 10.79 ± 7.05 | 4.45 ± 0.69 | 3.58 ± 3.31 | 2.12 ± 3.47 |
| Student's t v. A | — | 9.86*** | 4.29** | 2.64* | 5.18** | 1.91 | 3.45* | 1.1 | 1.58 |
| F: Compound C-30 + morphine | 10 mg/kg + (M) | 74.51 ± 9.7 | 66.53 ± 15.1 | 50.61 ± 15.5 | 47.53 ± 15.7 | 29.65 ± 12.1 | 34.24 ± 9.11 | 26.97 ± 10.04 | 71.81 ± 24.0 |
| Student's t v. A | — | 14.32*** | 8.67*** | 5.82** | 5.86** | 4.23** | 5.18** | 4.92** | 9.43*** |
| Student's t v. B | — | 2.23 | 2.00 | 2.16 | 3.2* | 2.69* | 4.79** | 4.42** | 6.96*** |
| G: Compound C-30 + Morphine | 10 mg/g + (M) | 44.52 ± 17.2 | 67.27 ± 9.6 | 67.31 ± 14.0 | 56.04 ± 8.55 | 49.48 ± 2.26 | 34.34 ± 10.34 | 27.50 ± 6.13 | 17.47 ± 8.07 |
| Student's t v. A | — | 5.11** | 13.78*** | 8.83*** | 12.54*** | 36.76*** | 6.18*** | 7.91*** | 4.47** |
| Student's t v. B | — | 1.31 | 2.35 | 3.84** | 6.51*** | 10.45*** | 5.76** | 6.86*** | 3.49** |

Note:
*($p < 0.05$)
**($p < 0.01$)
***($p < 0.001$)
Calculated straight lines of regression:
Group B: = Activity = −0.327 × hour + 48.41 (coeffic. of correlation = 0.95)
Group C: = Activity = −0.118 × hour + 45.08 (coeffic. of correlation = 0.76)
Group D: = Activity = −0.320 × hour + 67.97 (coeffic. of correlation = 0.93)
Group E: = Activity = −0.251 × hour + 66.47 (coeffic. of correlation = 0.89)
Group F: = Activity = −0.314 × hour + 70.38 (r = 0.96)
Group G: = Activity = −0.245 × hour + 66.06 (r = 0.79)

From the data given in Table 5 and from the calculated straight lines of regression, it may be seen that, from the third treatment up to the end of the experiment, the groups C-G were significantly more active than the group B treated solely with morphine.

Furthermore, after the fifth treatment, the morphine group was not significantly different from the control group, while the groups C-G maintained significant activity compared with the controls up to the final treatment after 168 hours.

From the calculation of the straight lines of regression, it may also be seen that, while the activity of the morphine group fell to 0 on the sixth day of treatment, the groups C-G reached the level of inactivity between the ninth and the sixteenth days.

The anti-CCK activity, the anti-spastic activity, and the choleretic activity of the compounds of the invention will now be illustrated.

ANTI-CCK ACTIVITY ON GUINEA PIG GALL BALDDERS IN VITRO

A longitudinal strip of guinea pig gall bladder was placed in a bath of isolated members in the presence of The isometric contractions were detected by means of a force transducer and recorded.

The gall bladder was made to contract with the use of a 10 ng/ml concentration of CCK-8; the antagonistic activity of the compounds of the invention on the contracting effect of the CCK was determined with the use of different concentrations and the ED 50 value, that is the concentration in μg/ml of a compound which could antagonise 50% of the contracting effect of the CCK, was determined.

The results obtained are set out in the following table which gives the compounds tested and the ED 50 values which were calculated by the regression method from a test of at least three experiments for each compound studied.

TABLE 6

In vitro anti-CCK-8 activity of the compounds of the invention (concentration used - 10 ng/ml) on guinea pig gall bladders, expressed as the ED 50 in μg/ml.

| COMPOUNDS | ACTIVITY ED50 (μg/ml) | COMPOUNDS | ACTIVITY ED50 (μg/ml) |
|---|---|---|---|
| Compound C-1 | >200 | Compound C-20 | >200 |

TABLE 6-continued

In vitro anti-CCK-8 activity of the compounds of the invention (concentration used - 10 ng/ml) on guinea pig gall bladders, expressed as the ED 50 in µg/ml.

| COMPOUNDS | ACTIVITY ED50 (µg/ml) | COMPOUNDS | ACTIVITY ED50 (µg/ml) |
|---|---|---|---|
| Compound C-2 | >200 | Compound C-21 | >200 |
| Compound C-3 | 34.4 | Compound C-22 | >200 |
| Compound C-4 | 1.1 | Compound C-23 | >200 |
| Compound C-5 | 4.2 | Compound C-24 | >200 |
| Compound C-6 | 0.33 | Compound C-25 | 30.3 |
| Compound C-7 | 0.06 | Compound C-26 | 146.5 |
| Compound C-8 | 0.93 | Compound C-27 | 10.2 |
| Compound C-9 | 7.40 | Compound D-1 | >200 |
| Compound C-10 | 43.7 | Compound D-2 | >200 |
| Compound C-11 | 0.85 | Compound D-3 | >200 |
| Compound C-12 | 64.7 | Compound D-4 | >200 |
| Compound C-13 | >200 | Compound D-5 | >200 |
| Compound C-14 | 118.4 | Compound D-6 | >200 |
| Compound C-15 | >200 | Compound D-7 | >200 |
| Compound C-16 | >200 | Compound D-8 | >200 |
| Compound C-17 | >200 | Compound D-9 | >200 |
| Compound C-18 | 60.3 | Compound D-10 | >200 |
| Compound C-19 | >200 | Compound D-11 | >200 |
| Compound C-28 | >300 | Compound C-36 | 13.4 |
| Compound C-29 | 262 | Compound C-42 | 50.1 |
| Compound C-30 | 33.5 | Compound C-47 | 35.1 |
| Compound C-31 | 22.9 | Compound C-48 | 119.1 |
| Compound C-32 | >300 | Compound D-12 | >300 |
| Compound C-33 | 131.7 | Compound D-15 | 245.0 |
| Compound C-34 | 40.1 | Compound D-17 | >300 |
| Compound C-35 | 367.1 | Compound C-54 | 1.2 |
|  |  | Compound C-55 | 0.5 |

From the data given in the table it is seen that the claimed compounds antagonise 50% of the activity of CCK-8 at a concentration which, for the more active compounds (such as, for example, the compound C-7), is only about 10 times greater than that of the specific antagonist, thus showing an extraordinary specificity of action.

In order to confirm the evidence of the studies in vitro several of the more interesting compounds were tested in vivo on guinea pig gall bladders in situ.

The method used is that described by Ljungberg (Svensk. Farm. Tidskr. 68, 351–354, 1964).

Guinea pigs having a weight of about 400 g, anaesthetised with urethane, were used; the substances under examination were administered intraveneously into the jugular vein.

The responses of the gall bladders to the substances under test were detected by means of a force transducer and recorded by means of a microdynamometer. The optimum contracting dose was chosen as 10 ng/kg of CCK-8. The antagonist compounds tested were administered in increasing doses so as to enable the calculation of an ED50 value, that is in the dose (in mg/kg i.v.) capable of inhibiting 50% of the contracting effect of 10 ng/kg i.v. of CCK-8.

The results obtained are given in Table 7 below, which gives the doses used and the effects obtained expressed as a percentage inhibition of the contracting effect of CCK-8 as well as the ED50 found.

TABLE 7

Anti-CCK-8 activity of several of the compounds of the invention (concentration used - 10 ng/kg) on guinea pig gall bladders in situ expressed as the ED50 in mg/kg i.v.

| COMPOUNDS | DOSE (mg/kg i.v.) | EXPERIMENT 1 | EXPERIMENT 2 | EXPERIMENT 3 | EXPERIMENT 4 | ED50 (mg/kg i.v.) r: (coeff. of correlation) |
|---|---|---|---|---|---|---|
| C-4 | 0.03 | — | — | −11.8 |  | 0.30 |
|  | 0.10 | −36.7 | −49.3 | −40.0 |  | (r: 0.90) |
|  | 0.30 | −44.6 | −68.4 | −51.7 |  | t = 5.46*** |
|  | 1.00 | −92.1 | −88.5 | — |  |  |
| C-6 | 0.01 | — | — | −12.9 |  | 0.05 |
|  | 0.03 | — | −49.7 | −40.0 |  | (r: 0.96) |
|  | 0.10 | −72.6 | −55.8 | −62.9 |  | t = 9.07*** |
|  | 0.30 | −97.0 | −82.8 | — |  |  |
|  | 1.00 | −100.0 | — | — |  |  |
| C-7 | 0.003 | — | — | −10.6 |  | 0.02 |
|  | 0.01 | −36.8 | −28.2 | −25.9 |  | (r: 0.98) |
|  | 0.03 | −62.1 | −57.0 | −59.2 |  | t = 13.9*** |
|  | 0.10 | −77.5 | −89.8 | −94.7 |  |  |
| Compound C-30 | 3 | 16.7 | 0 | 6.0 | — | 13.8 |
|  | 10 | 14.6 | 20.8 | 31.1 | — | Coefficient of correlation (r): 0.91 |
|  | 30 | 82.1 | 92.5 | 79.5 | — |  |
| Compound C-31 | 3 | 16.7 | 0 | 22.8 | — | 16.3 |
|  | 10 | 14.6 | 0 | 31.7 | — | (r): 0.80 |
|  | 30 | 82.1 | 92.5 | 58.7 | — |  |
| Compound C-36 | 1 | 4.3 | 15.7 | 32.7 | — | 5.1 |
|  | 3 | 30.0 | 12.1 | 40.0 | 20.3 | (r): 0.91 |
|  | 10 | 64.8 | 71.6 | 63.3 | 78.7 |  |
|  | 30 | — | — | — | 100 |  |

***P < 0.001

The results obtained essentially confirm what was previously seen in the in vitro experiments, that is, that several of the compounds of the invention are extremely powerful CCK antagonists which, even at doses as low as 0.1 mg/kg in the case of the compounds C-6 and C-7, can block gall bladder contractions induced by CCK-8 even at concentrations certainly higher than physiological concentrations.

The anti-spastic activity which the present compounds exert on the entire digestive system is also notable. Measured in mice with the vegetable carbon test (rate of transit through the stomach and the intestine), this activity is illustrated in the following table.

TABLE 8

Examples of anti-spastic activity for the compounds claimed administered intraperitoneally in mice. Values expressed as the ED 50 in mg/kg, that is the dose which reduces the intestinal transit of carbon by 50%

| COMPOUND | ANTISPASTIC ACTIVITY: ED50 mg/kg (i.p.) |
|---|---|
| Compound C-28 | 91.8 |

TABLE 8-continued

Examples of anti-spastic activity for the compounds claimed administered intraperitoneally in mice. Values expressed as the ED 50 in mg/kg, that is the dose which reduces the intestinal transit of carbon by 50%

| COMPOUND | ANTISPASTIC ACTIVITY: ED50 mg/kg (i.p.) |
|---|---|
| Compound C-30 | 77.7 |
| Compound C-34 | 65.5 |
| Compound C-35 | 180.9 |
| Compound C-36 | 208 |
| Compound C-37 | 160.1 |
| Compound C-41 | 182.4 |
| Compound C-46 | 66.9 |
| Compound C-4 | 38.8 |
| Compound C-6 | 29.5 |
| Compound C-7 | 16.8 |
| Compound C-20 | 77.5 |
| Compound C-27 | 40.3 |
| Compound D-2 | 50.7 |
| Compound D-5 | 74.9 |

A much more specific anti-spastic activity, that is adhering much more to a physiological situation, is illustrated by the following experiment.

The abdomen of an anaesthetised rabbit was cut open to show the transverse colon. A small balloon full of water was inserted at the point established and connected to a pressure transducer by means of a polythene cannula filled with water.

The optimum sensitivity was fixed in relation to the physiological conditions and the products were administered through the femoral vein. Contractions were induced by the administration of 100 ng/kg of CCK.

The activity of the product of the invention is illustrated in Table 9.

TABLE 9

Anit-spastic activity in the colon of rabbits stimulated by CCK-8.

| COMPOUNDS | DOSES (mg/kg iv) | EXPERIMENT 1 | EXPERIMENT 2 | EXPERIMENT 3 | ED50 (mg/kg iv) r: (coeff. of correlation |
|---|---|---|---|---|---|
| C-6 | 0.1 | 0 | — | — | ED50 = 1.53 |
| | 0.3 | −24.1 | −14.9 | −8.5 | r = 0 943 |
| | 1 | −57.9 | −45.0 | −41.8 | t = 8.05(***) |
| | 3 | −91.7 | −77.5 | −81.6 | |
| C-7 | 0.1 | 0 | — | −10.7 | ED50 = 1.11 |
| | 0.3 | −19.1 | −36.8 | −21.8 | r = 0.919 |
| | 1 | −42.6 | −74.2 | −64.5 | t = 6.58(***) |
| | 3 | −100.0 | −100.0 | — | |

(***)P < 0,001

The data given indicate that several of the tested compounds which are subject of the present invention are also antagonistic, as already shown for the gall bladder, towards intestinal contractions induced by CCK administered at high doses (100 ng/kg).

The anti-spastic activity is shown at very low doses of between 1-3 mg/kg for the best of the compounds used.

A further interesting characteristic of these compounds is that they increase biliary flow considerably.

The following experiment was carried out: a cannula was inserted in the bile duct of a rat anaesthetised with urethane, together with a small needle connected to a polythene tube, and the bile liquid was thus collected. The collection was carried out for one hour before the intravenous administration of the tested compounds and for a further two hours after administration, the samples collected at 30 minute intervals being weighed.

In order to prevent possible dehydration of the animals, 0.5 ml of physiological solution was administered at 30 minute intervals up to a total of 3 ml.

The results obtained for several of the compounds of the invention are given in the following table expressed as the ED 50, that is the quantity of substance in mg/kg i.v. capable of causing a 50% increase in the biliary flow after the treatment with the drugs (average value determined over the 2 hour period) with respect to control values (average value determined during one hour of collection before the treatment with the drugs).

From the data given it may be inferred that the compounds in question have a powerful choleretic activity; on average the ED 50 for the compounds tested was 5-25 mg/kg i.v. and there was a remarkable correspondence between the dose and the pharmocological response (the coefficients of correlation were in fact greater than 0.90 in all cases).

TABLE 10

Percentage variation in the biliary flow in rats induced by several compounds of the invention.

| COMPOUNDS | DOSES (mg/kg i.v.) | EFFECT (% increase with respect to controls) | ED50 (mg/kg i.v.) r = (coeff. of correlation) |
|---|---|---|---|
| Compound C-6 | 3 | +40.4 | 4.2 |
| | 10 | +69.8 | (r = 0.93) |
| | 30 | +88.7 | |
| Compound C-20 | 12.5 | +48.5 | 19.4 |
| | 25.0 | +63.9 | (r = 0.98) |
| | 50.0 | +108.0 | |
| Compound D-11 | 12.5 | +33.7 | 18.5 |
| | 25.0 | +80.0 | (r = 0.98) |
| | 50.0 | +118.8 | |
| Compound C-30 | 12.5 | +33.7 | 18.5 |
| | 25 | +60.2 | (r = 0.99) |
| | 50 | +121.2 | |
| | 100 | +197.8 | |
| Compound C-35 | 12.5 | +9.6 | 29.5 |
| | 25.0 | +51.9 | (r = 0.98) |
| | 50.0 | +91.9 | |
| | 100 | +159.7 | |
| Compound C-36 | 12.5 | +15.5 | 26.75 |
| | 25.0 | +48.5 | (r = 0.99) |
| | 100.0 | +215.8 | |

In order to check the hypothesis that the anti-CCK activity shown by most of the compounds in question may be used to advantage in the treatment of anorexia in man or as an appetite stimulant for farm animals, the following experiment was carried out:

Male rats having a weight of about 160 g, divided into groups of 10 animals, were used. Each group was given the drug daily, in the doses indicated, for 3 weeks.

The drug, in the form of the sodium salt, was dissolved in water and administered in a volume of 10 ml of H₂O/kg while the control group received an equal volume of the solvent alone.

The following tables give the average values of the food consumption and the average weight of each group of animals, calculated weekly as well as the Student's t value calculated from the various treated groups and the group of control animals.

From the data given in Tables 11 and 12 it may be seen that daily doses of 0.3 mg/kg of the compound C-7 induced an increase of about 15% in the food consumption compared with the controls; this increase was about 30% for the other doses tested and was at all times highly significant.

The weight increase of the animals treated compared with the weight increase of the control animals took a similar course; all the groups treated with C-7 gave a significantly greater weight increase than the control animals for all the times studied.

adenocarcinoma. Five days after the inoculation the animals were divided at random into 4 groups of 10 animals each, that is, a control group, a group of animals treated with 10 μg/kg of CCK-8 three times a day, a group of animals treated with 5 mg/kg i.p. of compound C-7 three times a day, and a fourth group treated simultaneously with the compound C-7 and CCK-8 in the manner described above.

After 15 days of this treatment, the animals were killed, and the normal pancreas and the inoculated pancreatic tumours in the cheek pouches were collected and weighed. The DNA was extracted and measured according to conventional techniques.

The results thus obtained are given in Table 13, expressed as mean values ($\pm$S.E.)

The data given in the table show that the cholecystokinin hormone (of which CCK-8 is the biologically active component), which has a trophic action on nor-

TABLE 11

Determination of the body weight (in g) of various groups measured at different times

| GROUPS | DOSE (mg/kg os) | TIME 0 | WEEK 1 | WEEK 2 | WEEK 3 | WEEK 4 |
|---|---|---|---|---|---|---|
| A: Control | — | 166.1 ± 4.5 | 197.4 ± 3.8 | 238.6 ± 4.09 | 280.0 ± 3.94 | |
| B: Compound C-7 | 0.3 | 162.1 ± 2.48 | 201.3 ± 2.7 | 254.5 ± 2.66 | 315.2 ± 2.72 | |
| Student's t vsA | | 0.78 | 0.83 | 3.26** | 7.33*** | |
| C: Compound C-7 | 1 | 166.0 ± 1.56 | 214.7 ± 1.93 | 267.5 ± 2.6 | 319.8 ± 2.49 | |
| Student's t vsA | | 0.021 | 4.06** | 5.96*** | 8.53*** | |
| D: Compound C-7 | 3 | 166.6 ± 1.73 | 227.9 ± 1.65 | 290.9 ± 2.6 | 349.5 ± 2.82 | |
| Student's t vsA | | 0.1 | 7.11*** | 11.3*** | 14.32*** | |
| Control | — | 254.2 ± 7.71 | 278.9 ± 7.02 | 308.8 ± 4.7 | 352.6 ± 2.09 | 383.1 ± 2 |
| Compound C-30 | 3 | 270.8 ± 8.3 | 310.2 ± 7.01 | 380.5 ± 6.5 | 409.7 ± 2.99 | 437.3 ± 55 |
| Student's t | | t = 1.464 | t = 3.14** | t = 8.992*** | t = 15.66*** | t = 9.24*** |
| Compound C-30 | 10 | 271.4 ± 9.3 | 332.9 ± 5.7 | 383.2 ± 6.5 | 439.1 ± 4.3 | 470.5 ± 6.5 |
| Student's t VsA | | t = 1.427 | t = 5.981*** | t = 9.19*** | t = 18.234*** | t = 12.798*** |
| Compound C-30 | 30 | 267.9 ± 7.7 | 315.7 ± 7.4 | 371.9 ± 7.9 | 437.1 ± 5.2 | 488.1 ± 6.4 |
| Student's t VsA | | t = 1.252 | t = 3.606** | t = 6.82*** | t = 15.108*** | t = 15.668 |

Note:
**($p < 0.01$)
***($p < 0.001$)

TABLE 12

Food consumption (in g/week) in the various groups treated determined at different times.

| GROUPS | DOSE (mg/kg os) | WEEK 1 | WEEK 2 | WEEK 3 | WEEK 4 |
|---|---|---|---|---|---|
| A: Control | — | 166.1 ± 1.87 | 197.6 ± 1.96 | 208.7 ± 2.16 | |
| B: Compound C-7 | 0.3 | 176.4 ± 3.70 | 216.8 ± 4.71 | 239.3 ± 4.07 | |
| Student's t vsA | | 2.5* | 3.75** | 6.72*** | |
| C: Compound C-7 | 1 | 199.6 ± 3.88 | 230.5 ± 3.09 | 261.4 ± 4.24 | |
| Student's t vsA | | 7.78*** | 8.99*** | 11.2*** | |
| D: Compound C-7 | 3 | 198.4 ± 3.66 | 244.8 ± 3.09 | 268.8 ± 4.86 | |
| Student's t vsA | | 7.87*** | 12.87*** | 12.68*** | |
| Control | — | 174.3 ± 5.07 | 209.6 ± 5.01 | 175.4 ± 4.34 | 180.3 ± 3.78 |
| Compound C-30 | 3 | 193.7 ± 3.58 | 233.2 ± 4.56 | 187.1 ± 8.40 | 204.0 ± 3.63 |
| Student's t vsA | | t = 3.128** | t = 3.482** | t = 1.237N.S | t = 4.527*** |
| Compound C-30 | 10 | 219.8 ± 5.62 | 264.3 ± 5.61 | 234.5 ± 5.05 | 234.6 ± 3.99 |
| Student's t vsA | | t = 6.012*** | t = 7.273*** | t = 8.875*** | t = 9.884*** |
| Compound C-30 | 30 | 233.7 ± 5.45 | 267.9 ± 4.92 | 247.0 ± 5.19 | 244.5 ± 4.06 |
| Student's t vsA | | t = 7.982*** | t = 8.307*** | t = 10.582*** | t = 11.655*** |

Note:
*($p < 0.05$)
**($p < 0.01$)
***($p < 0.001$)
N.S. (not significant)

Inhibiting action on the growth of a pancreatic adenocarcinoma induced by CCK-8

The anti-cholecystokinin effect of the most powerful of the compounds which are the subject of the present invention, that is the compound C-7, on the trophic activity of CCK on normal pancreatic cells and on those of a pancreatic adenocarcinoma is to be studied.

Male hamsters were inoculated in the cheek pouches with a suspension of $1 \times 10^5$ tumoral cells of a pancreatic mal pancreatic cells, also stimulates the growth of a pancreatic adenocarcinoma. The compound C-7, a powerful specific CCK antagonist, antagonises both these actions of CCK-8 in a higly significant manner.

The experimental data given above appear to provide an indication for believing that the use of the compound C-7 or other anti-cholecystokinin compounds which are the subject of the invention will have particularly favourable results in the treatment of tumours sustained by endogenous bioactive polypeptides (in particular CCK), such as gastro-intestinal and pancreatic tumours.

The experimental data given above also appears to provide an extensive indication that the use of the drugs of

TABLE 13

Inhibiting action of Compound C-7 on the growth of normal and tumoral pancreatic cells, induced by CCK-8

| TREATMENT | No. of Animals | DOSE | Pancreas weight (mg) | student's t | PANCREATIC DNA (mg) | student's t |
|---|---|---|---|---|---|---|
| A: CONTROL | 10 | — | 380 ± 29.7 | — | 0.8 ± 0.10 | — |
| B: CCK-8 | 8(') | 10 mcg/kg (3 times per day) | 600 ± 54.1 | 3.76() | 1.5 ± 0.11 | 4.72(*) |
| C: COMPOUND C-7 | 10 | 5 mg/kg (3 times per day) | 336 ± 22.6 | 1.18 | 0.93 ± 0.09 | 1.03 |
| D: COMPOUND C-7 + CCK-8 | 10 | 10 mcg/kg CCK-8 + 5 mg/kg C-7 | 374 ± 25.4 | vsA: 0.15 vsB: 4.05(*) | 1.0 ± 0.08 | vsA: 1.53 vsB: 3.61() |

| TREATMENT | No. of Animals | DOSE | Weight of Pancreatic Carcinoma (mg) | student's t | TUMORAL DNA (mg) | student's t |
|---|---|---|---|---|---|---|
| A: CONTROL | 10 | — | 113 ± 7.66 | — | 0.4 ± 0.05 | — |
| B: CCK-8 | 8(') | 10 mcg/kg (3 times per day) | 180 ± 15.2 | 4.17(***) | 0.7 ± 0.13 | 2.79(*) |
| C: COMPOUND C-7 | 10 | 5 mg/kg (3 times per day) | 104 ± 7.5 | 0.86 | 0.42 ± 0.02 | 0.34 |
| D: COMPOUND C-7 + CCK-8 | 10 | 10 mcg/kg CCK-8 + 5 mg/kg C-7 | 109.5 ± 6.2 | vsA: 0.37 vsB: 4.64(***) | 0.4 ± 0.02 | vsA: 0 vsB: 2.51(*) |

(')2 animals died during the treatment
(*)P < 0.05
(**)P < 0.01
(***)P < 0.001 the invention in association with morphine or other analgesic drugs (whether narcotic or not) is a considerable therapeutic innovation which can make available to the doctor compounds of pre-eminent interest for the treatment of pain of any etiology. This treatment would appear to be particularly indicated in the case of prolonged administrations of opiates where there is a very great need for the drug not to cause habituation, or at least for this to be maintained within acceptable limits. Furthermore, their possible use in the detoxication of patients who have become dependent from the prolonged use of opiate drugs would appear to be of enormous therapeutic and social interest.

The experimental data given above also show the utility of these compounds in the treatment of various pathological conditions concerning the gastro-intestinal system, for example in spastic syndromes and in pain relief in general and in particular in the treatment of biliary diskinesia and irritable colon.

One may also keep in mind the powerful anti-CCK activity exhibited by many of the compounds in question, a favourable therapeutic use in the treatment of anorexia or in some pathological conditions of the SNC linked to imbalances in the physiological neuron levels of the CCK or other bio-active peptides.

We claim:

1. Pharmaceutically active derivatives of D,L-glutamic acid and D,L-aspartic acid having the formulae:

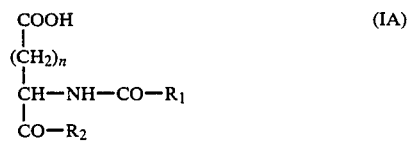

(IA)

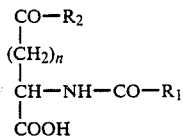

(IB)

in which n is equal to 1 or 2, $R_1$ is a phenyl group mono-, di- or tri-substituted with linear or branched $C_1$–$C_4$ alkyl groups, which may be the same or different, or with halogens, with a cyano group or a trifluoromethyl group, and in which $R_2$ is selected from the group consisting of morpholino, piperidino and amino with one or two linear, branched or cyclic alkyl group substituents containing from 1 to 8 carbon atoms, which may be the same or different, and pharmaceutically-acceptable salts thereof.

2. A compound derived from glutamic acid according to claim 1, of formula (IA), in which n is equal to 2, $R_1$ is selected from the group consisting of 3,4-dimethyl-phenyl and 3,4-dichloro-phenyl, and $R_2$ is an amino group bi-substituted with linear $C_4$–$C_5$ alkyl groups, and pharmaceutically-acceptable salts thereof.

3. A compound derived from glutamic acid according to claim 1, of formula (IB), in which n is equal to 2, $R_1$ is a 4-cyano-phenyl group and $R_2$ is an amino group bi-substituted with linear $C_4$–$C_5$ alkyl groups, and pharmaceutically-acceptable salts thereof.

4. A pharmaceutical preparation comprising a compound according to claim 1 or a pharmaceutically-acceptable salt thereof and a pharmaceutically-acceptable carrier.

5. Pharmaceutically active derivatives of D,L-glutamic acid having the formulae:

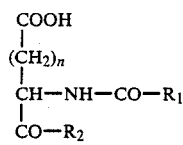

or pharmaceutically acceptable salts thereof, in which n is equal to 2, $R_1$ is selected from the group consisting of 3,4-dimethyl-phenyl and 3,4-dichloro-phenyl, and $R_2$ is an amino group di-substituted with linear $C_4$–$C_5$ alkyl groups.

6. Pharmaceutically active derivatives of D,L-glutamic acid having the formulae:

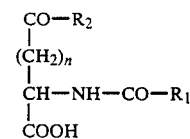

or pharmaceutically acceptable salts thereof, in which n is equal to 2, $R_1$ is a 4-cyano-phenyl group and $R_2$ is an amino group di-substituted with linear $C_4$–$C_5$ alkyl groups.

* * * * *